(12) United States Patent
Matsumoto et al.

(10) Patent No.: US 11,439,435 B2
(45) Date of Patent: Sep. 13, 2022

(54) STAGE DEVICE, MINUTE OPERATION DEVICE, AND METHOD OF CONTROLLING SAME

(71) Applicant: CANON KABUSHIKI KAISHA, Tokyo (JP)

(72) Inventors: Toru Matsumoto, Hiratsuka (JP); Hitoshi Nishitani, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 336 days.

(21) Appl. No.: 16/703,183

(22) Filed: Dec. 4, 2019

(65) Prior Publication Data
US 2020/0179005 A1    Jun. 11, 2020

(30) Foreign Application Priority Data

Dec. 6, 2018 (JP) .............................. JP2018-228914
Dec. 6, 2018 (JP) .............................. JP2018-228915
Feb. 4, 2019 (JP) .............................. JP2019-017988

(51) Int. Cl.
*A61B 17/43* (2006.01)
*C12M 1/26* (2006.01)
(Continued)

(52) U.S. Cl.
CPC ................ *A61B 17/43* (2013.01); *B25J 7/00* (2013.01); *B25J 19/0025* (2013.01); *C12M 33/08* (2013.01)

(58) Field of Classification Search
CPC ......... A61B 17/43; B25J 7/00; B25J 19/0025; C12M 33/08
See application file for complete search history.

(56) References Cited

U.S. PATENT DOCUMENTS

| 2008/0213899 A1* | 9/2008 | Olgac | C12M 35/00 435/455 |
| 2013/0023052 A1* | 1/2013 | Tanaka | G02B 21/32 435/461 |
| 2015/0111297 A1* | 4/2015 | Cohen | C12N 15/89 435/455 |

FOREIGN PATENT DOCUMENTS

| JP | H08-290377 A | 11/1996 |
| JP | 3363510 B2 | 1/2003 |

(Continued)

OTHER PUBLICATIONS

Journal of Clinical Embryologist, vol. 19, No. 2 (2017), pp. 126 to 128, Shimpei Mizuta, cited in the Specification in paragraph [0002]. Original JP document and partial translation.

(Continued)

*Primary Examiner* — Samuel G Gilbert
(74) *Attorney, Agent, or Firm* — Cowan, Liebowitz & Latman, P.C.

(57) ABSTRACT

A stage device capable of performing piercing vibration and translational driving by using one actuator, and performing very low-speed driving in the translational driving with high accuracy. The stage device includes an X stage having a vibration actuator that includes an vibration element and a contact body, one of which is a movable body connected to an object to be driven, and drives the object to be driven in an X-axis direction, and a control section that controls driving of the vibration actuator. The control section causes two-phase AC voltages to be applied to an electromechanical energy conversion element to thereby excite predetermined vibrations in the vibration element, to drive the vibration actuator by switching between a movement mode for moving the object to be driven in the X-axis direction and a vibration mode for vibrating the object to be driven in the X-axis direction.

9 Claims, 17 Drawing Sheets

(51) Int. Cl.
*B25J 19/00* (2006.01)
*B25J 7/00* (2006.01)

(56) References Cited

FOREIGN PATENT DOCUMENTS

| JP | 4811358 B2 | 11/2011 |
| JP | 2012-16107 A | 1/2012 |
| JP | 6174616 B2 | 8/2017 |

OTHER PUBLICATIONS

"Assisted Reproductive Technology Text" written by Yasuhisa Araki, published on Jan. 2015, by Ishiyaku Publishers, Inc., pp. 91 to 93, Yasuhisa Araki, cited in the Specification in paragraph [0004], Original JP document and partial translation.

\* cited by examiner

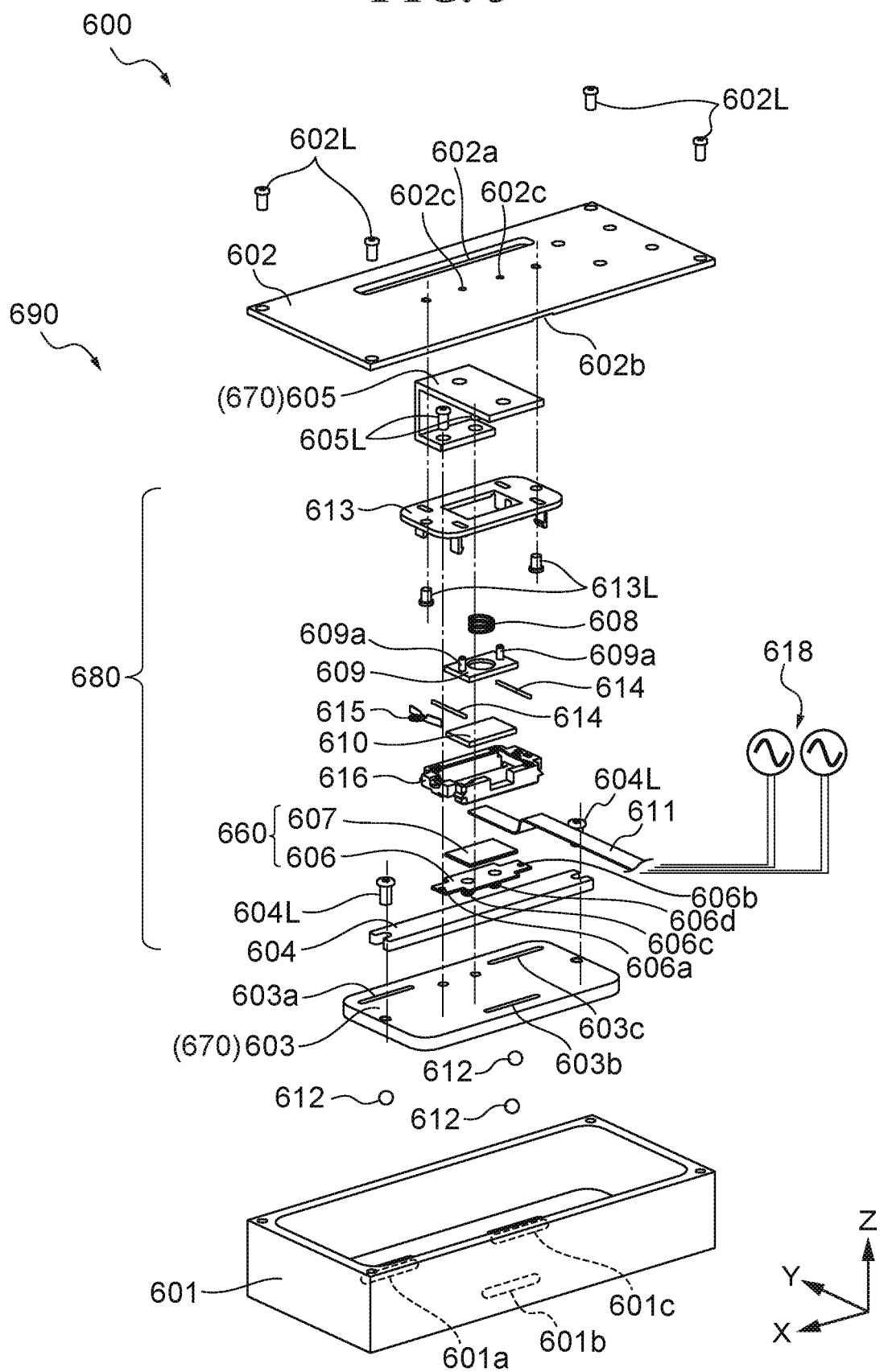

FIG. 4A
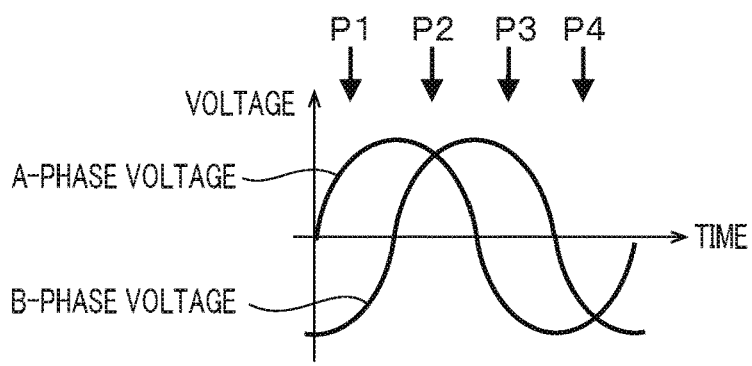
FIG. 4B  FIG. 4C  FIG. 4D
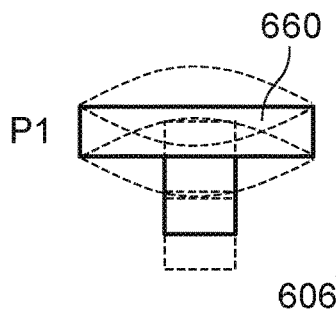 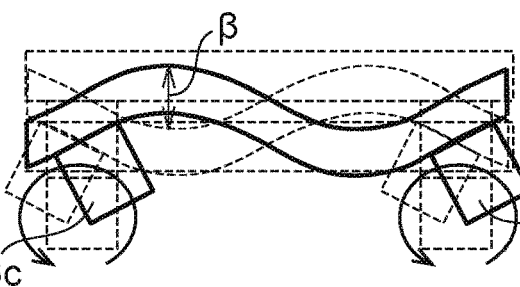 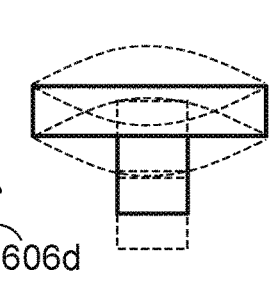
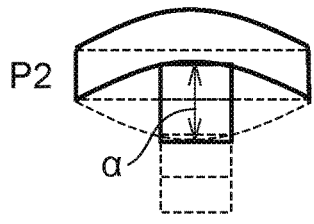 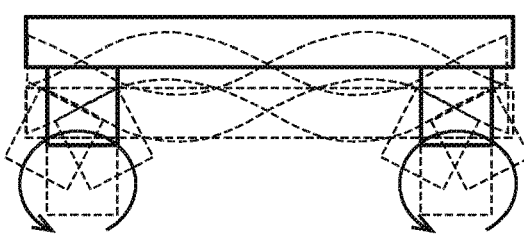 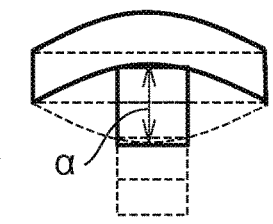
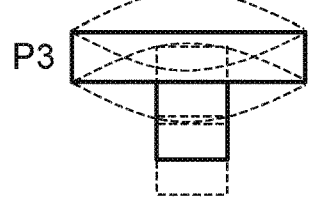 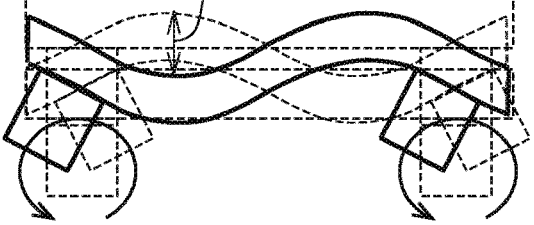
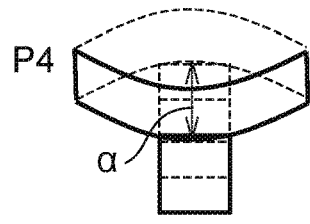 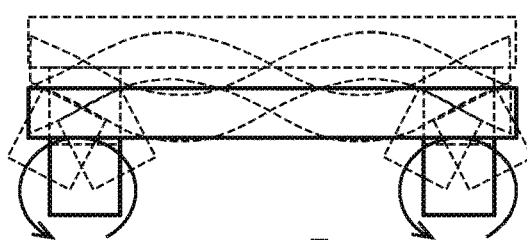 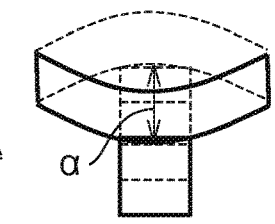

FIG. 5A
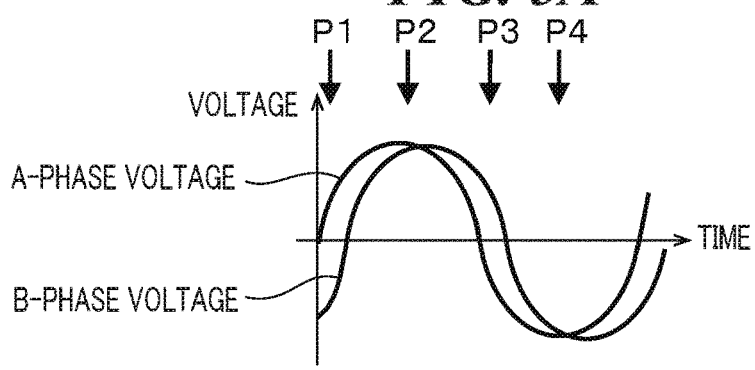
FIG. 5B
P1 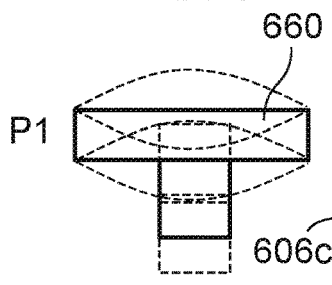
P2 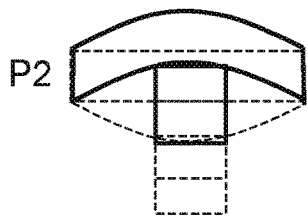
P3 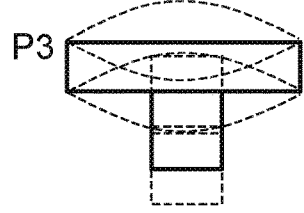
P4 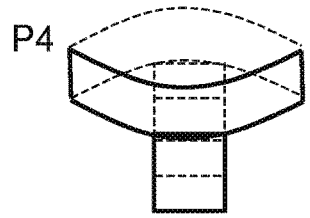
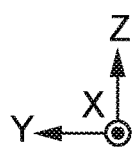
FIG. 5C
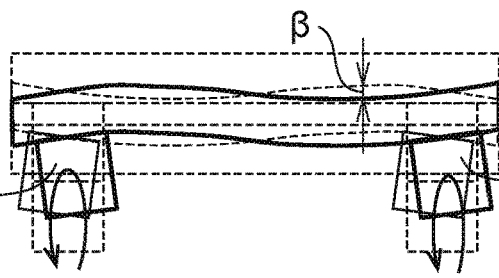
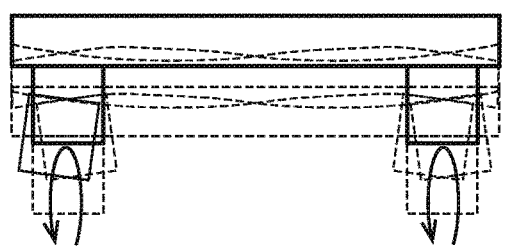
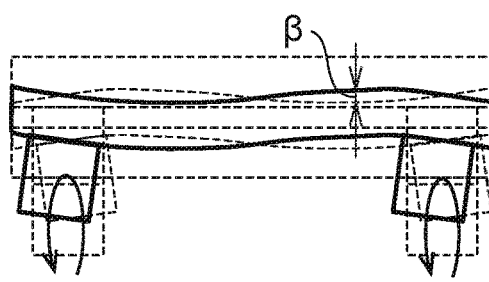
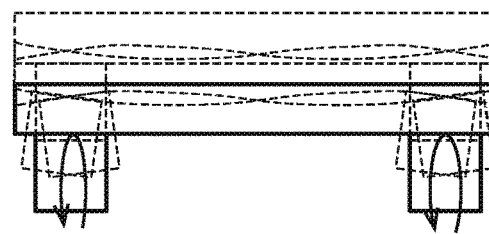
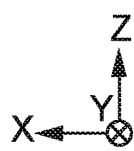
FIG. 5D
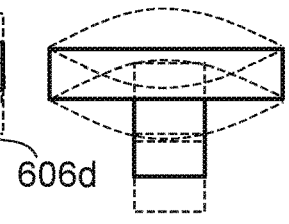
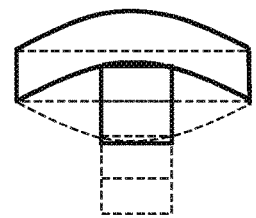
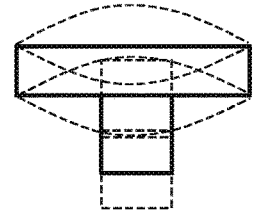
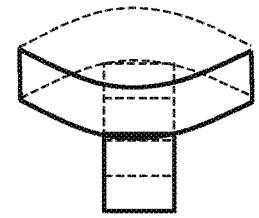
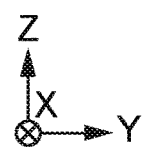

STAGE DEVICE, MINUTE OPERATION DEVICE, AND METHOD OF CONTROLLING SAME

BACKGROUND OF THE INVENTION

Field of the Invention

The present invention relates to a stage device, and a minute operation device and a method of controlling the same, and more particularly to a device useful in a field of assisted reproductive technology.

Description of the Related Art

In the field of assisted reproductive technology, as a method of directly injecting a sperm into an ovum, there is known Intracytoplasmic Sperm Injection (hereinafter referred to as the "ICSI"). In the ICSI, a piercing vibration device for breaking an ovum cell membrane by piercing-vibrating an injection pipette, and a stage device for moving the injection pipette forward and backward are used (see Shimpei Mizuta, Journal of Clinical Embryologist, Vol. 19, No. 2 (2017), pp. 126 to 128)

FIG. 14A shows a conventional injector device 2000. The injector device 2000 includes a cylinder 2001, a piston 2002, a female screw portion 2003 provided in the cylinder 2001, a male screw portion 2004 provided on the piston 2002, and a dial part 2005 provided at an end of the male screw portion 2004 on a side opposite to the piston 2002. The female screw portion 2003 provided in the cylinder 2001 and the male screw portion 2004 provided on the piston 2002 are engaged with each other, and hence when the dial part 2005 is manually rotated, the piston 2002 is moved forward/backward relative to the cylinder 2001. Further, the cylinder 2001 is connected to an injection pipette 1002, appearing in FIG. 14B, via a tube 2006. This enables the injector device to handle the amount of forward/backward movement of liquid within the pipette via the tube.

In "Assisted Reproductive Technology Text" written by Yasuhisa Araki, published on January, 2015, by Ishiyaku Publishers, Inc., pp. 91 to 93, a method of breaking an ovum cell membrane of an ovum, which is one of processes of the method of ICSI, is disclosed. FIG. 14B shows the ovum cell membrane breaking method in the conventional embodiment in the order of a step (B1) to a step (B6). Q1 to Q6 each represent a time of each step.

A solid line L1001 indicates the position of a tip end point of the injection pipette 1002. A solid line L1002 indicates an amount of forward/backward movement of a liquid 1005 in the injection pipette 1002, and a solid line L1003 indicates an operation amount of the injector device 2000. The operation amount L1003 is e.g. a rotational angle of the dial part 2005. The movement of the liquid in the injection pipette 1002 is referred to as the forward/backward movement amount L1002 of the liquid 1005 and is the same as the movement of a sperm 1004 floating in the liquid 1005. The sign of the forward/backward movement amount L2 of the liquid 1005 is plus when the liquid 1005 advances toward an ovum 1001 in the injection pipette 1002. The sign of the operation amount L1003 of the injector device 2000 is plus when the injector device 2000 is operated to advance the liquid 1005 in the plus direction, i.e. toward the ovum 1001.

First, in the step (B1) in FIG. 14B, the sperm 1004 is sucked into the injection pipette 1002 together with the liquid 1005, such as a polyvinylpyrrolidone (PVP) solution, for making it easy to handle the sperm. Then, the injection pipette 1002 having sucked the sperm 1004 therein is moved close to the ovum 1001 held by a holding pipette 1003 (Q1).

Next, in the step (B2) in FIG. 14B, an operator manually operates the injector device 2000 in the plus direction to move the sperm 1004 close to the tip end point of the injection pipette 1002 with the liquid 1005 (Q2).

Next, in the step (B3) in FIG. 14B, the operator presses the injection pipette 1002 into an ovum cell 1001a to an illustrated degree using a micromanipulator, not shown (Q3). At this time, a transparent body 1001d around the ovum cell 1001a is broken by the injection pipette 1002.

Then, as the process proceeds from the step (B3) to the step (B4) in FIG. 14B, the operator manually operates the dial part 2005 of the injector device 2000 so as to move the liquid 1005 in the injector pipette 1002 backward (from Q3 to Q4). With this operation, an ovum cell membrane 1001b is sucked into the injection pipette 1002, and it is possible to break the ovum cell membrane 1001b.

In the step (B4) in FIG. 14B, the operator visually confirms breakage of the ovum cell membrane 1001b (Q4). After visually confirming breakage of the ovum cell membrane 1001b, the operator manually operates the dial part 2005 in a reverse direction to move the liquid 1005 toward the ovum 1001. Then, the operator continues to operate the dial part 2005 until the sperm 1004 is moved out of the injection pipette 1002 and enters an ovum cell cytoplasm 1001c (from Q4 to Q5).

In the (B5) in FIG. 14B, when it can be confirmed that the sperm 1004 has entered the ovum cell cytoplasm 1001c, the operator stops operating of the dial part 2005 (Q5).

Finally, the operator draws the injection pipette 1002 out from the ovum 1001 to a state shown in the (B6) in FIG. 14B, and terminates the operation (Q6).

In these operations, the forward/backward movement amount L1002 of the liquid 1005 in the injection pipette 1002 changes in proportion to the operation amount L1003 of the dial part 2005 of the injector device 2000.

Further, FIG. 8 is a diagram useful in explaining an operation procedure of the ICSI using a conventional piercing vibration device. The piercing vibration device is equipped with the injection pipette 1002. The piercing vibration device equipped with the injection pipette 1002 is driven in a state held by a stage device (not shown). Further, processing for discharging the sperm 1004 held in the injection pipette 1002 and a transparent body 1001dz entered the injection pipette 1002, from the injection pipette 1002 is performed by an injector device (not shown). In FIG. 8, a solid line XL1 and a solid line XL2 indicate a movement amount of the injection pipette 1002 and an operation amount of the stage device, respectively. Further, a solid line XL3 and a solid line XL4 indicate an on/off operation of a switch of the piercing vibration device and an operation amount of the injector device for moving the sperm 1004, the transparent body 1001dz, and so forth, forward/backward, respectively.

In a step X1, an operator operates the stage device in a state in which the ovum 1001 is held by the holding pipette 1003 to move the injection pipette 1002 holding the sperm 1004 close to the ovum 1001. When the process proceeds from the step X1 to a step X2, the operator operates the stage device to press the tip end point of the injection pipette 1002 against the transparent body 1001d. Then, in the step X2, the operator turns on the piercing vibration device to vibrate the injection pipette 1002 and thereby break the transparent body 1001d. Note that the movement amount of the injection pipette 1002, which corresponds to an amplitude of piercing vibration of the injection pipette 1002, is very small compared with the movement amount of the injection pipette 1002, which is caused by translational driving by the stage device. In FIG. 8, the movement amount of the injection pipette 1002, moved for piercing vibration, is illustrated in an exaggerated manner.

In a step X3, the operator operates the stage device to separate the injection pipette 1002 from the ovum 1001. At this time, the transparent body 1001*dz* broken in the step X2 has entered the injection pipette 1002. Then, in a step X4, the operator operates the injector device to discharge the transparent body 1001*dz* from the injection pipette 1002, and then move the sperm 1004 to the tip end point of the injection pipette 1002.

In a step X5, the operator drives the stage device to press the injection pipette 1002 into the ovum cell membrane 1001*b* by a certain length. Note that the ovum cell 1001*a* has a structure in which the outside of the ovum cell cytoplasm 1001*c* is covered with the ovum cell membrane 1001*b*. Thus, the operator turns on the piercing vibration device in a state in which the injection pipette 1002 has been pressed in against the ovum cell membrane 1001*b* to break the ovum cell membrane 1001*b*. In a step X6 after confirming breakage of the ovum cell membrane 1001*b*, the operator operates the injector device to inject the sperm 1004 into the ovum cell cytoplasm 1001*c*. In a step X7 after completing injection of the sperm 1004 into the ovum cell cytoplasm 1001*c*, the operator operates the stage device to draw the injection pipette 1002 out of the ovum 1001. This completes the series of processing operations.

As an example of this piercing vibration device for executing the above-described ICSI, Japanese Patent No. 6174616 describes the configuration for performing piercing vibration of the injection pipette by driving a piezoelectric element. Further, Japanese Patent No. 4811358 describes the configuration for performing translational driving and vibration driving using one actuator.

However, the technique described in Japanese Patent No. 6174616 cannot make it possible for one actuator to cannot execute the operation of breaking the ovum cell membrane 1001*b* and the operation of advancing/retreating the injection pipette 1002 into/from the ovum cell 1001*a*. Further, the technique described in Japanese Patent No. 4811358 uses a stick-slip type vibration actuator. Here, in the operation of advancing/retreating the injection pipette 1002 into/from the ovum cell 1001*a*, it is necessary to drive the injection pipette 1002 at a very low speed. However, the stick-slip type vibration actuator has a large dead band and is not suitable for the very low-speed driving.

SUMMARY OF THE INVENTION

The present invention provides a stage device that is capable of performing piercing vibration and translational driving by using one actuator, and also performing very low-speed driving with high accuracy in translational driving.

In a first aspect of the present invention, there is provided a stage device comprising a vibration actuator including a vibration element having an elastic body and an electromechanical energy conversion element, and a contact body in contact with the vibration element, one of the vibration element and the contact body being fixed at a predetermined position, and the other being a movable body which is movable in a predetermined direction and is also connected to an object to be driven, the vibration actuator being configured to drive the object to be driven in the predetermined direction, and a control unit configured to perform control such that the movable body is moved or vibrated in the predetermined direction by applying two-phase AC voltages to the electromechanical energy conversion element to excite predetermined vibrations in the vibration element, wherein the control unit causes the vibration actuator to be driven such that the operation mode is switched between a movement mode for moving the object to be driven in the predetermined direction and a vibration mode for vibrating the object to be driven in the predetermined direction.

In a second aspect of the present invention, there is provided a minute operation device comprising an object to be driven, a vibration actuator including a vibration element having an elastic body and an electromechanical energy conversion element, and a contact body in contact with the vibration element, one of the vibration element and the contact body being fixed at a predetermined position, and the other being a movable body which is movable in a predetermined direction and is also connected to the object to be driven, the vibration actuator being configured to drive the object to be driven in the predetermined direction, and a control unit configured to perform control such that the movable body is moved or vibrated in the predetermined direction by applying two-phase AC voltages to the electromechanical energy conversion element to excite predetermined vibrations in the vibration element, wherein the control unit causes the vibration actuator to be driven such that the operation mode is switched between a movement mode for moving the object to be driven in the predetermined direction and a vibration mode for vibrating the object to be driven in the predetermined direction.

In a third aspect of the present invention, there is provided a method of controlling a minute operation device that drives a vibration actuator including a vibration element having an elastic body and an electromechanical energy conversion element, and a contact body in contact with the vibration element, one of the vibration element and the contact body being fixed at a predetermined position, and the other being a movable body which is movable in a predetermined direction and is also connected to an object to be driven, to thereby drive the object to be driven in the predetermined direction, the method comprising moving the object to be driven to a predetermined position by driving the movable body through application of two-phase AC voltages to the electromechanical energy conversion element to thereby excite predetermined vibrations in the vibration element, and vibrating, in a state in which the object to be driven is in the predetermined position, the object in the predetermined position in the predetermined direction through application of two-phase AC voltages to the electromechanical energy conversion element to thereby vibrate the vibration element in the predetermined direction.

According to the present invention, the stage device is capable of performing piercing vibration and translational driving by using one actuator and also performing very low-speed driving with high accuracy in translational driving.

Further features of the present invention will become apparent from the following description of exemplary embodiments (with reference to the attached drawings).

BRIEF DESCRIPTION OF THE DRAWINGS

FIG. 3 is an exploded perspective view showing a structure of the X stage.

FIGS. 4A to 4D are diagrams schematically showing vibrations excited in a vibration element in a case where a phase difference between an A-phase voltage and a B-phase voltage is set to 90°.

FIGS. 5A to 5D are diagrams schematically showing vibrations excited in the vibration element in a case where the phase difference between the A-phase voltage and the B-phase voltage is set to 30°.

DESCRIPTION OF THE EMBODIMENTS

The present invention will now be described in detail below with reference to the accompanying drawings showing embodiments thereof. Here, a manipulator system used for assisted reproductive technology will be described as an example of a minute operation device including a stage device according to the present invention. However, the stage device and the minute operation device according to the present invention are not limited to these.

Figure 1:
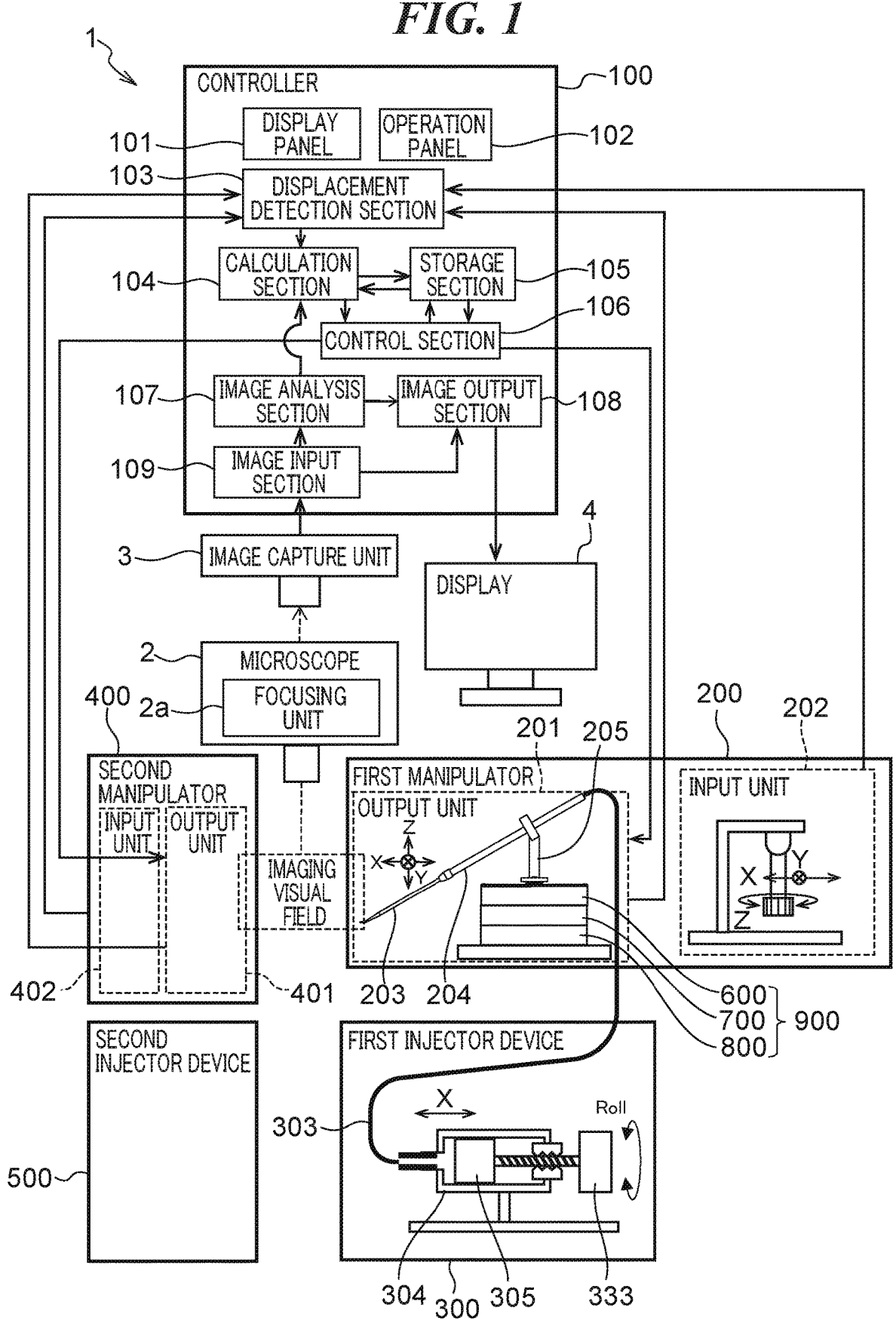
FIG. 1 is a block diagram useful in explaining the general configuration of a manipulator system according to a first embodiment.

FIG. 1 is a block diagram showing the general configuration of a manipulator system 1 according to a first embodiment of the present invention. The manipulator system 1 includes a microscope 2, an image capture unit 3, a display 4, a controller 100, a first manipulator 200, a first injector device 300, a second manipulator 400, and a second injector device 500.

The microscope 2 includes a focusing unit 2a configured to adjust the focus on an ovum and a sperm, an injection pipette 203 of the first manipulator 200, a holding pipette 403 of the second manipulator 400 (see FIG. 7), etc., during an ICSI operation. The image capture unit 3 includes an image capture device, such as a CMOS sensor, that captures an image through an optical system of the microscope 2, and captures respective images of an ovum, a sperm, the injection pipette 203, the holding pipette 403, etc. The images captured by the image capture device 3 are input to an image input section 109 of the controller 100.

The controller 100 includes a display panel 101, an operation panel 102, the image input section 109, an image analysis section 107, an image output section 108, a displacement detection section 103, a calculation section 104, a storage section 105, and a control section 106. The operation panel 102 includes a dial, switches, a foot pedal, and so forth, none of which are shown, for inputting control parameters used by the control section 106. The display panel 101 displays the control parameters set on the operation panel 102, a driving mode, referred to hereinafter, etc. Note that by forming the display panel 101 as a touch panel, it is possible to use the display panel 101 as one operation unit forming the operation panel 102.

An image sent from the image capture unit 3 is input to the image input section 109. The image input to the image input section 109 is sent to the image analysis section 107 and the image output section 108. The image analysis section 107 analyzes the image obtained by the image capture unit 3. A result of the analysis, obtained by the image analysis section 107, is sent to the calculation section 104 and the image output section 108. The image output section 108 outputs a result of analysis, sent from the image analysis section 107, and the image, sent from the image input section 109, to the display 4. The display 4 displays the image, sent from the image output section 108, and when displaying the image on the display 4, it is possible to more precisely express an object to be observed by the microscope 2 by displaying the image in combination with the result of analysis, sent from the image analysis section 107. Note that it is also possible to remotely operate the first manipulator 200 and the like, while viewing the display 4.

The displacement detection section 103 detects displacements of an output unit 201 and an input unit 202 of the first manipulator 200, and displacements of an output unit 401 and an input unit 402 of the second manipulator 400. Results of displacement detection, detected by the displacement detection section 103, are sent to the calculation section 104. The calculation section 104 performs predetermined calculation based on the result of analysis, acquired from the image analysis section 107, the results of displacement detection, acquired from the displacement detection section 103, and information read from the storage section 105. A result of the calculation, obtained by the calculation section 104, is sent to the control section 106 and the storage section 105.

The control section 106 outputs a drive amount determined based on the result of calculation, sent from the calculation section 104, and the information, read from the storage section 105, to the output unit 201 of the first manipulator 200 and the output unit 401 of the second manipulator 400. The storage section 105 stores the result of calculation, sent from the calculation section 104, and the drive amount determined by the control section 106. Further, the storage section 105 can also store information acquired from the components other than the calculation section 104 and the control section 106 (such as an image input to the image input section 109, a result of analysis performed by the image analysis section 107, displacement amounts detected by the displacement detection section 103, and an input amount input to the operation panel 102).

Figure 8:
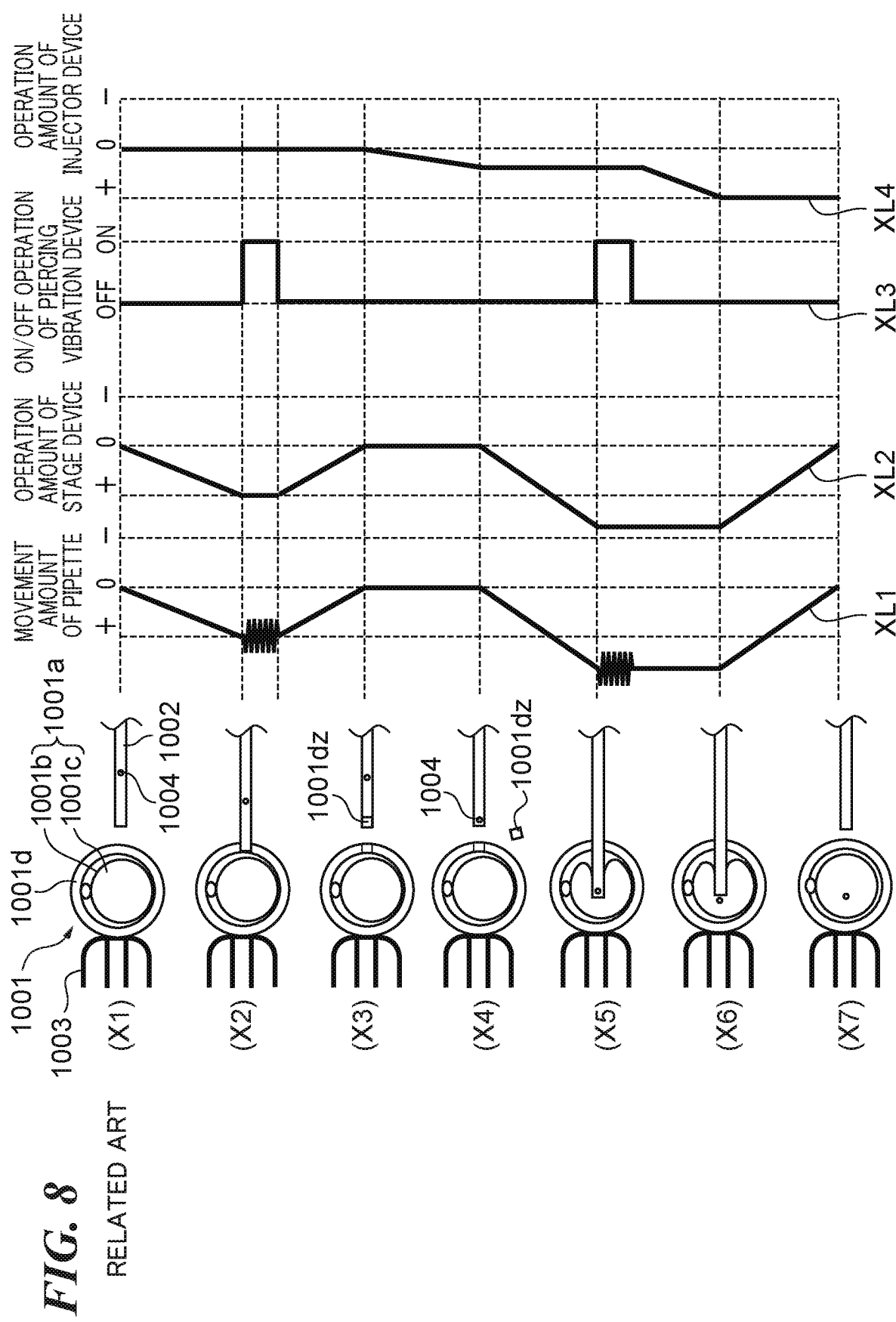
FIG. 8 is a diagram useful in explaining an operation procedure of ICSI using a conventional piercing vibration device.

The first manipulator 200 has the output unit 201 and the input unit 202. The output unit 201 includes a stage device 900 and objects to be driven by the stage device 900, and the objects to be driven refer to the injection pipette 203, an injection pipette holder 204, and a holder supporting part 205, in the present embodiment. As described above with reference to FIG. 8, an object to be processed, such as a sperm, is filled in the injection pipette 203. The stage device 900 includes a Z stage 800 which can be driven in a Z-axis direction, a Y stage 700 which can be driven in a Y-axis direction, and an X stage 600 which can be driven in an X-axis direction. Definition of the X-axis direction, the Y-axis direction, and the Z-axis direction will be described hereinafter.

The input unit 202 includes an input device (such as a joystick) supporting movement of the stage device 900 in each of the X-axis direction, the Y-axis direction, and the Z-axis direction. The operation amount for translational driving of the stage device 900 can be input in a value which continuously changes via the input device, and the input operation amount is detected by the displacement detection section 103. By thus operating the input unit 202, it is possible to operate the stage device 900 in a mode for translationally driving the stage device 900. Note that the input unit 202 may be one capable of multi-stage input with such a degree of resolution as will not cause a problem of performance.

In the output unit 201, the holder supporting part 205 is disposed on the stage device 900, the injection pipette holder 204 is supported by the holder supporting part 205, and the injection pipette 203 is held by the injection pipette holder 204. The stage device 900 has a displacement sensor (displacement measuring unit (not shown)) for measuring displacement in each of the X-axis direction, the Y-axis direction, and the Z-axis direction. Note that an axial direction of the tip end portion of the injection pipette 203 is defined as the X-axis direction, an optical axis direction of the microscope 2 (axial direction of the holder supporting part 205) is defined as the Z-axis direction, and a direction orthogonal to the X-axis direction and the Z-axis direction is defined as the Y-axis direction.

An output signal from the displacement sensor in the stage device 900 is sent to the displacement detection section 103, and is used for controlling the output unit 201 of the first manipulator 200. Note that the method of controlling the stage device 900 based on the input amount input to the input unit 202 and the actual drive amount in the stage device 900 (such as PID control) is well known, and hence detailed description is omitted. Thus, in the first manipulator 200, it is possible to control the injection pipette 203 such that it can be positioned in the X-axis direction, the Y-axis direction, and the Z-axis direction. Details of the configuration of the stage device 900 will be described hereinafter.

The first injector device 300 includes a cylinder 304, a piston 305 that can adjust the capacity by advancing and retreating within the cylinder 304, and an operation section 333 that can drive the piston 305 to advance and retreat the same. One end of a tube 303 is connected to the cylinder 304. Further, the other end of the tube 303 is connected to the injection pipette 203 via the injection pipette holder 204 of the first manipulator 200. With this, the first injector device 300 can move an object to be injected, such as a sperm, filled in the injection pipette 203 forward/backward by operating the operation section 333 to advance and retreat the piston 305.

The second manipulator 400 includes the output unit 401 and the input unit 402. The second manipulator 400 is different from the first manipulator 200 in that the holding pipette 403 (see FIG. 7) is included in place of the injection pipette 203, but is the same in the other respects of the configuration, and hence illustration and description thereof is omitted. The holding pipette 403 holds an object to be processed (such as the ovum 1001 appearing in FIG. 7).

The second injector device 500 including an input unit 502 and an output unit 503 has the same configuration as that of the first injector device 300, and hence illustration thereof is omitted. Note that a tube (not shown) included in the second injector device 500 connects between a cylinder (not shown) and the holding pipette 403 of the second manipulator 400, and this enables the inner pressure operation of the holding pipette 403.

Next, the configuration of the stage device 900 will be described in detail. In the stage device 900, at least the X stage 600 is provided with a linear moving unit using a vibration actuator as a drive source, which drives the injection pipette 203 in the X-axis direction. On the other hand, although the Y stage 700 and the Z stage 800 may use a linear moving unit having a vibration actuator as a drive source, this is not limitative, but a linear moving unit having a stepping motor or a voice coil motor as a drive source may be used.

Figure 2:
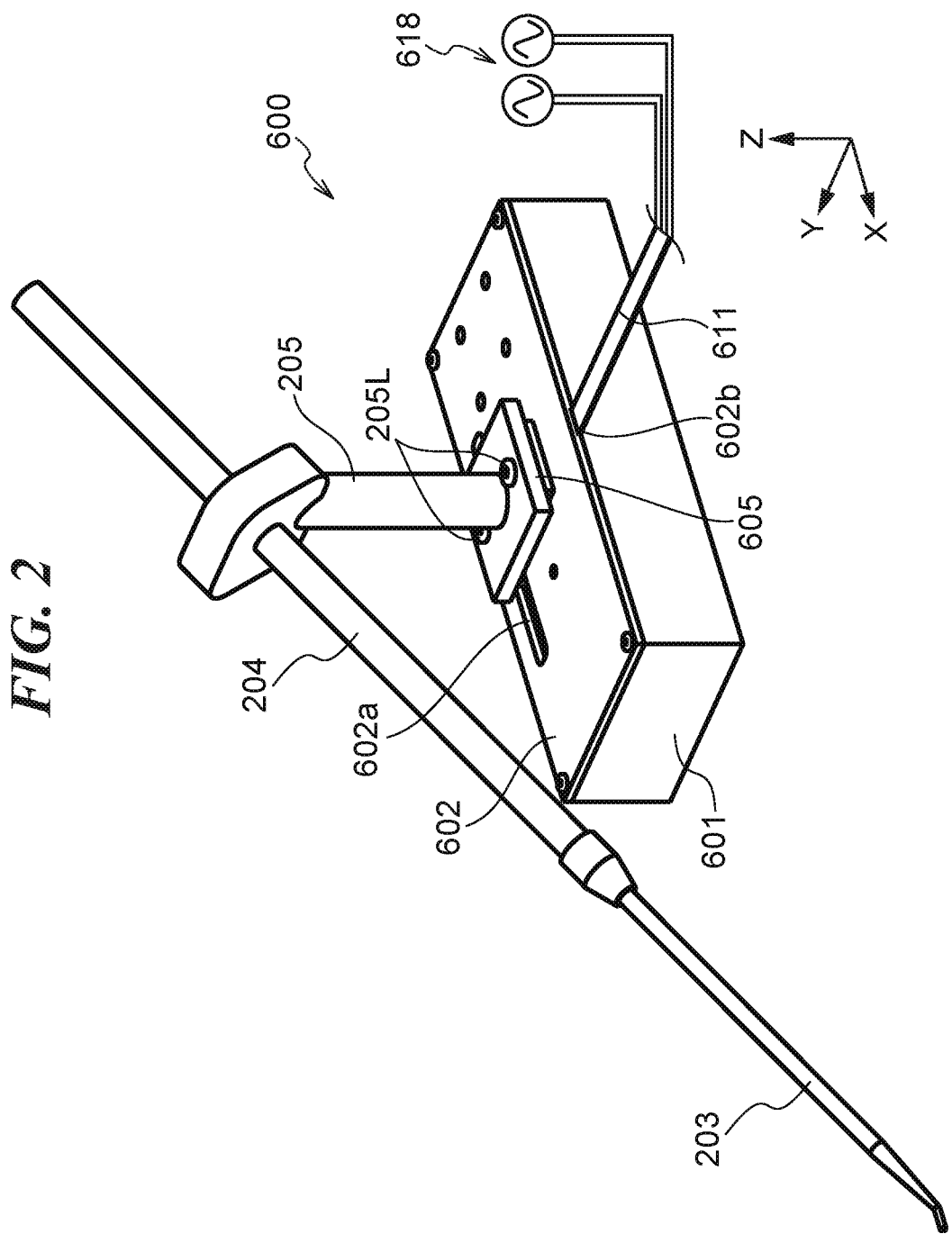
FIG. 2 is an appearance perspective view of an X stage of an output unit of a first manipulator.

FIG. 2 is an appearance perspective view of the output unit 201, from which the Y stage 700 and the Z stage 800 are omitted. FIG. 3 is an exploded perspective view of the X stage 600. The X stage 600 includes a casing 601 and a cover 602 as fixed portions, which are immovable, and has the linear moving unit, denoted by reference numeral 690, arranged therein. The cover 602 is fixed to the casing 601 with screws 602L. The linear moving unit 690 includes a vibration actuator 680 and a movable unit 670.

The vibration actuator 680 includes a contact body 604, a pressurizing member 608, a pressure force transmission member 609, a shock-absorbing member 610, an actuator holder 613, rolling rollers 614, a rolling roller spring 615, and a vibration element holder 616. A vibration element 660 includes an elastic body 606 and a piezoelectric element 607 (electromechanical energy conversion element).

The actuator holder 613 is fixed to the cover 602 with screws 613L. The vibration element holder 616 is supported by the actuator holder 613 via the rolling rollers 614 and the rolling roller spring 615. With this, the actuator holder 613 supports the vibration element holder 616 without looseness in the X-axis direction and is movable in the Z-axis direction.

The vibration element 660 includes the elastic body 606 and the piezoelectric element 607, and the piezoelectric element 607 is fixed to the elastic body 606 e.g. by means of adhesion. The elastic body 606 is a thin plate-like component formed of metallic material, such as stainless steel, and includes connection portions 606a and 606b, and protrusions 606c and 606d (see FIG. 4B), protruding toward the contact body 604. Respective parts of the connection portions 606a and 606b are fixed to the vibration element holder 616 e.g. by means of adhesion. That is, the vibration element 660 is supported by the actuator holder 613 fixed to the cover 602 via the vibration element holder 616. Therefore, the vibration actuator 680 is configured such that the contact body 604 moves in the X-axis direction relative to the vibration element 660, the arrangement position of which is fixed, as described hereinafter.

The contact body 604 is fixed to a movable base 603 as a component of the movable unit 670 with screws 604L at opposite end portions thereof in the X-axis direction, and the contact body 604 and the movable unit 670 can move in the X-axis direction in unison. The contact body 604 is in contact with tip ends of the protrusions 606c and 606d formed on the elastic body 606. The pressurizing member 608 generates a pressure force for bringing the vibration element 660 into contact with the contact body 604. The pressure force transmission member 609 includes two protrusions 609a slidably inserted through holes 602c formed in the cover 602, and is guided in the Z-axis direction. The pressure force transmission member 609 is arranged between the vibration element 660 and the pressurizing member 608, and transmits a pressure force applied from the pressurizing member 608 to the vibration element 660.

The shock-absorbing member 610 is arranged between the pressure force transmission member 609 and the piezoelectric element 607, and is used for transmitting a force of the pressurizing member 608 to the vibration element 660 without attenuating the force. Note that the shock-absorbing member 610 is fixed to the pressure force transmission member 609 e.g. by mean of adhesion. Two-phase AC voltage 618 are applied to the piezoelectric element 607 via a wiring board 611. The wiring board 611 is mounted on a surface of the piezoelectric element 607 on a side toward the shock-absorbing member 610, and is drawn out from a groove 602b formed in the cover 602 to the outside of the X stage 600.

The movable unit 670 includes the movable base 603 and a movable plate 605. The movable plate 605 is arranged such that a wall portion, parallel to the Z-axis direction, is inserted in an opening 602a formed in the cover 602, and two wall portions, orthogonal to the Z-axis direction (hereinafter referred to as the "upper surface portion" and the "lower surface portion"), are opposed to each other across the cover 602. The lower surface portion of the movable plate 605 is fixed to the movable base 603 with screws 605L, and the holder supporting part 205 is fixed to the upper surface portion with screws 205L.

The movable base 603 is formed with three movable guiding portions 603a, 603b, and 603c, each extending in the X-axis direction. On the other hand, the casing 601 as the fixed part is formed with fixed guiding portions 601a, 601b, and 601c in a manner opposed to the movable guiding portions 603a, 603b, and 603c, respectively. Further, three rolling balls 612 are sandwiched between the movable guiding portions 603a, 603b, and 603c and the fixed guiding portions 601a, 601b, and 601c, respectively, such that the movable base 603 and the movable plate 605 can be guided in the X-axis direction in unison.

Next, a method of driving the X stage 600 by driving the vibration actuator 680 to thereby drive the injection pipette 203 in the X-axis direction will be described. The two-phase AC voltages 618, which can be changed in at least one of the phase difference and the frequency, are applied to the piezoelectric element 607 to generate predetermined vibrations in the vibration element 660. With this, it is possible to move the contact body 604 and the movable unit 670, which are the movable bodies arranged in a manner movable in the X-axis direction, relative to the fixed vibration element 660. Details of this mechanism have been described in Japanese Patent No. 3363510, Japanese Laid-Open Patent Publication (Kokai) No. 2012-16107, and forth, and hence description thereof is omitted. In the X stage 600, the movable unit 670 is moved along the movable guiding portions 603a to 603c in the X-axis direction.

The control section 106 drives the vibration element 660 (movable unit 670) in a movement mode M1 and a vibration mode M2. The movement mode M1 is a driving mode for moving the injection pipette 203 connected to the movable unit 670, forward/backward in the X-axis direction. The vibration mode M2 is a driving mode for vibrating the injection pipette 203 connected to the movable unit 670, in the X-axis direction (forward/backward moving direction).

The movement mode M1 will be described in detail. In the movement mode M1, the phase difference between the two-phase AC voltages (an A-phase voltage and a B-phase voltage) is set to +90° or −90°. Note that the piezoelectric element 607 has a common electrode (full-surface electrode) formed on one surface thereof (surface adhering to the elastic body 606) orthogonal to the Z-axis, and two independent electrodes (an A-phase electrode and a B-phase electrode), which are divided in the X-axis direction, provided on the other surface thereof orthogonal to the Z-axis. The A-phase voltage is an AC voltage applied to the A-phase electrode, the B-phase voltage is an AC voltage applied to the B-phase electrode, and the common electrode is used as a ground (earth) electrode.

FIGS. 4A to 4D are diagrams schematically showing vibrations excited in the vibration element 660 in a case where the AC voltages are applied to the piezoelectric element 607 by delaying the phase of the B-phase voltage from the A-phase voltage by approximately +90°. FIG. 4A is a diagram useful in explaining the A-phase voltage and the B-phase voltage. In FIG. 4A, timings P1, P2, P3, and P4, different from each other, for explaining vibrations excited in the vibration element 660 are defined. In FIG. 4B, front views of the vibration element 660 (as viewed from a positive direction of the X-axis (+X direction)) show respective states corresponding to the timings P1 to P4. In FIG. 4C, side views of the vibration element 660 (as viewed from a negative direction of the Y-axis (−Y direction)) show respective states corresponding to the timings P1 to P4. In FIG. 4D, rear views of the vibration element 660 (as viewed from a negative direction of the X-axis) showing respective states corresponding to the timings P1 to P4. Note that in FIGS. 4A to 4D, the connection portions 606a and 606b of the elastic body 606 and the piezoelectric element 607 are omitted from illustration.

At the timings P2 and P4 at which the A-phase voltage and the B-phase voltage are voltages of the same sign, the A-phase electrode and the B-phase electrode of the piezoelectric element 607 extend and compress in the same manner (when one extends within a X-Y plane, the other also extends), and a displacement c in a primary bending vibration in a short side direction (Y-axis direction) becomes maximum. At the timings P1 and P3 at which the A-phase voltage and the B-phase voltage are voltages of different signs, the A-phase electrode and the B-phase electrode extend and compress in an opposite manner (when one extends within the X-Y plane, the other compresses), and hence a displacement 3 in a secondary bending vibration in a longitudinal direction (X-axis direction) becomes maximum. The displacements shown in FIGS. 4B to 4D are continuously generated, and as a result, a circular motion (or elliptical motion) in a counterclockwise direction, shown in FIG. 4C, is generated on each of the protrusions 606c and 606d. By generating this circular motion (or elliptical motion) of the protrusions 606c and 606d, it is possible to obtain thrust (frictional drive force) for moving the contact body 604 and the movable unit 670 in the negative direction of the X-axis. Note that in a case where the AC voltages are applied to the piezoelectric element 607 by delaying the phase of the A-phase voltage from the B-phase voltage by approximately +90°, a circular motion in a clockwise direction, opposite from the direction of the circular motion shown in FIG. 4C, is generated. With this, it is possible to obtain thrust (frictional drive force) for moving the contact body 604 and the movable unit 670 in the positive direction of the X-axis.

FIGS. 5A to 5D are diagrams schematically showing vibrations excited in the vibration element 660 in a case where the AC voltages are applied to the piezoelectric element 607 by delaying the phase of the B-phase voltage from the A-phase voltage by approximately +30°. Note that FIGS. 5A to 5D correspond to FIGS. 4A to 4D, respectively. In a case where the phase difference between the A-phase voltage and the B-phase voltage is 30°, a time period in which the voltages of different signs are applied to the A-phase electrode and the B-phase electrode is short, and hence the displacement 3 in the secondary bending vibration in the X-axis direction becomes smaller than in the case where the phase difference between the A-phase voltage and the B-phase voltage is 90°. As a result, an elliptical motion, which is vertically long in the Z-axis direction, is generated on each of the protrusions 606c and 606d, and hence lower-speed driving in the X-axis direction is enabled, compared with the case where the phase difference between the A-phase voltage and the B-phase voltage is set to approximately +90° (FIGS. 4A to 4D). Note that it is possible to further generate an elliptical motion, which is vertically long in the Z-axis direction, by making the phase difference between the A-phase voltage and the B-phase voltage close to 0°, very low-speed driving is enabled. That is, the vibration actuator 680 can be referred to as the actuator capable of performing very low-speed driving with high accuracy.

Next, details of the vibration mode M2 will be described. In the vibration mode M2, the phase difference between the A-phase voltage and the B-phase voltage is set to +180° or −180°, or the vicinity of +180° or −180°. FIGS. 6A to 6D are diagrams schematically showing vibrations excited in the vibration element in a case where the AC voltages are applied to the piezoelectric element 607 by delaying the phase of the B-phase voltage from the A-phase voltage by approximately +180°. Note that FIGS. 6A to 6D correspond to FIG. 4A to 4D, respectively.

Figure 6A:
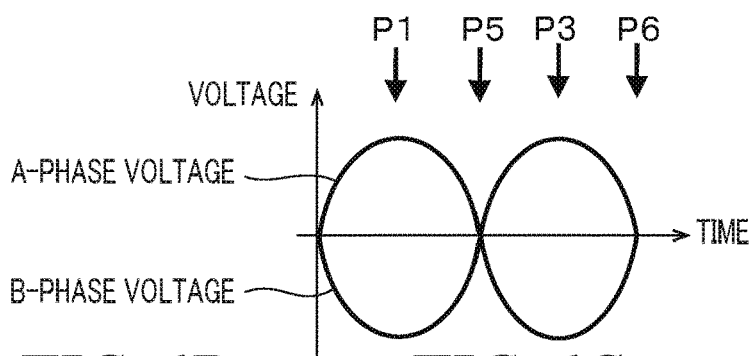
FIGS. 6A to 6D are diagrams schematically showing vibrations excited in the vibration element in a case where the phase difference between the A-phase voltage and the B-phase voltage is set to 180°.
Figures 6B, 6C, 6D:
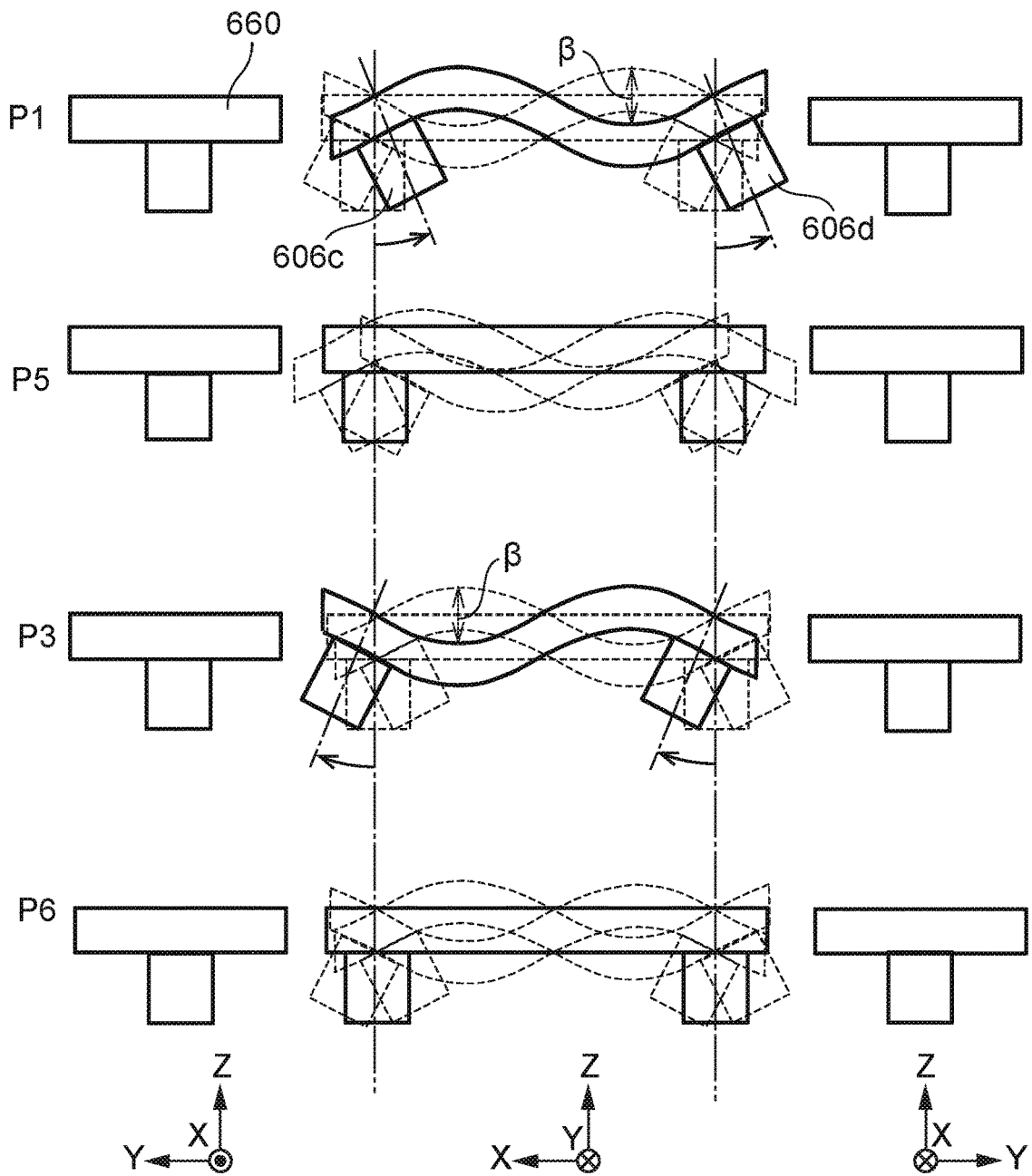

In a case where the phase difference is approximately 180°, timings P5 and P6 occur at which the A-phase voltage and the B-phase voltage both become equal to zero (0) Further, the voltages of the same sign are not applied, differently from the case of the timings P2 and P4 shown in FIGS. 4A to 4D and 5A to 5D, and hence as shown in FIGS. 6B and 6D, the primary bending vibration in the Y-axis direction is not generated. In the vibration element 660, only the displacement β in the second bending vibration in the X-axis direction (see FIG. 6C) is generated by applying the voltages of the different signs, as applied at the timings P1 and P3. As a result, the protrusions 606c and 606d do not perform a circular motion or an elliptical motion, but perform reciprocating motion in the X-axis direction to apply thrust (frictional drive force) for frictionally driving the contact body 604, whereby the contact body 604 is vibrated in the X-axis direction. At this time, by changing the magnitude (voltage value) of the A-phase voltage and the B-phase voltage to change the magnitude of deformation generated on the vibration element 660, it is possible to adjust the amount (amplitude) of displacement generated on the protrusions 606c and 606d in the X-axis direction.

Note that the A-phase voltage and the B-phase voltage, different in frequency between the movement mode M1 and the vibration mode M2, may be applied to the piezoelectric element 607. In the movement mode M1, the frequency is adjusted such that the primary bending vibration in the Y-axis direction and the secondary bending vibration in the X-axis direction are both generated. Further, in the vibration mode M2, the frequency is set such that only the secondary bending vibration in the X-axis direction is generated without generating the primary bending vibration in the Y-axis direction, and hence it is possible to apply the AC voltage of the frequency different from that in the movement mode M1. Note that the magnitude (voltage value), the phase difference, and the frequency of the two-phase AC voltages applied in the movement mode M1 and the vibration mode M2 can be set by using e.g. the switch and the dial, provided on the operation panel 102.

Examples of the operation method of driving the vibration element 660 in the vibration mode M2 include an operation method of switching on/off of the switch, provided on the operation panel 102, a foot pedal (not shown), or the like. Alternatively, an dedicated switch (not shown) for executing the vibration mode M2 may be provided in the input unit 202 of the first manipulator 200. In this case, the driving may be configured such that vibration continues while the dedicated switch is on, or vibration is generated only for a time period set in advance by one turning-on operation. During execution of the vibration mode M2, this state can be displayed on the display panel 101 or the display 4.

Figure 7:
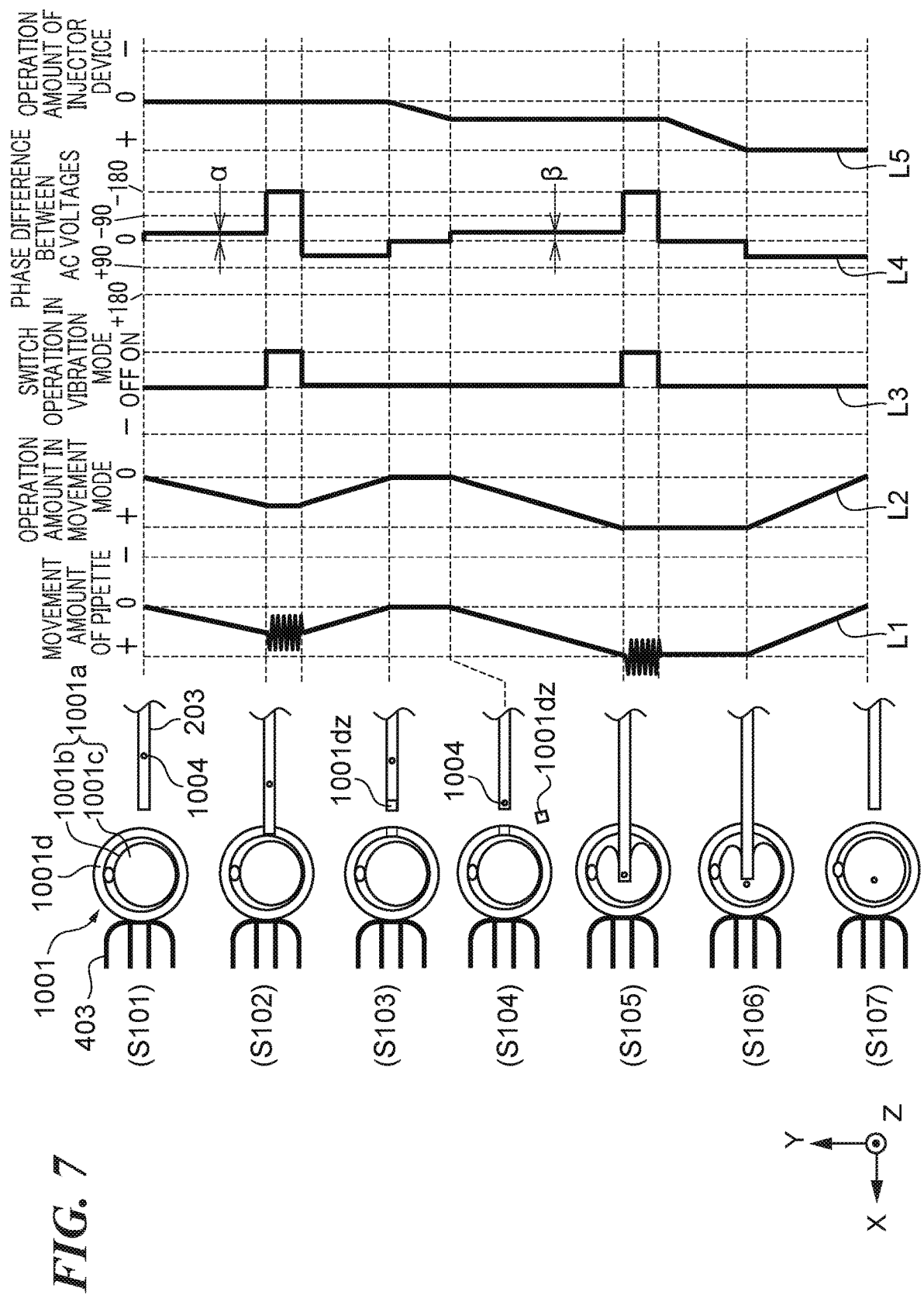
FIG. 7 is a diagram useful in explaining an operation procedure of ICSI using the manipulator system according to the first embodiment.

FIG. 7 is a diagram useful in explaining an operation procedure of ICSI using the manipulator system 1. In FIG. 7, a solid line L1 indicates the movement amount of the injection pipette 203. Here, the movement amount (vibration amplitude) in the vibration mode M2 is very small compared with the movement amount in the movement mode M1, and hence FIG. 7 shows the vibration amplitude in the vibration mode M2 in an exaggerated manner with respect to the movement amount in the movement mode M1. A solid line L2 indicates the operation amount of the input unit 202 of the first manipulator 200, in other words, the operation amount in the movement mode M1. A solid line L3 indicates the on/off operation of the switch for driving the injection pipette 203 in the vibration mode M2. A solid line L4 indicates the phase difference between the two-phase AC voltages (A-phase voltage and B-phase voltage) applied to the vibration element 660. A solid line L5 indicates the operation amount of the first injector device 300, for moving the sperm 1004, the transparent body 1001dz, etc., forward/backward in the X-axis direction.

A step S101 shows a state in which the holding pipette 403 holds the ovum 1001, and further, the injection pipette 203 having sucked the sperm 1004 therein has been moved close to the ovum 1001. Note that the state shown in the step S101 is a state in which the movable unit 670 has been moved in the positive direction of the X-axis by driving the vibration element 660 in the movement mode M1 from a state in which the injection pipette 203 was further spaced from the holding pipette 403. The phase difference between the A-phase voltage and the B-phase voltage applied to the piezoelectric element 607 at that time can be set e.g. to 90°.

When the process proceeds from the step S101 to a step S102, the operator operates the input unit 202 of the first manipulator 200 to drive the vibration element 660 in the movement mode M1 to thereby move the movable unit 670 in the positive direction of the X-axis at a very low speed.

At this time, the phase difference between the A-phase voltage and the B-phase voltage applied to the piezoelectric element 607 is set to a value close to 0°, whereby it is possible to drive the injection pipette 203 (movable unit 670) in the positive direction of the X-axis at the very low speed. This makes it possible to press the tip end point of the injection pipette 203 against the transparent body 1001d.

As described above, in a case where the tip end point of the injection pipette 203 is apart from the ovum 1001 by a certain distance or more, the injection pipette 203 is driven in the X-axis direction using the low-speed driving in the movement mode M1. In doing this, the phase difference may be continuously or stepwise changed within a range in which the absolute value of the phase difference between the A-phase voltage and the B-phase voltage is larger than 0° and also not larger than 90° such that the phase difference becomes smaller as the distance between the tip end point of the injection pipette 203 and the ovum 1001 is smaller. Further, when the tip end point of the injection pipette 203 is within a range of a certain distance from the ovum 1001, the injection pipette 203 is driven in the X-axis direction using the very low-speed driving in the movement mode M1. Note that the phase difference c between the AC voltages, illustrated in the operation from the step S101 to the step S102 is a very small phase difference, and hence it is illustrated in an exaggerated manner.

In the step S102, in the state in which the injection pipette 203 is pressed against the transparent body 1001d, the operator turns on the operation switch of the vibration mode M2 to drive the vibration element 660 in the vibration mode M2 to thereby break the transparent body 1001d by vibrating the movable unit 670 in the X-axis direction. In the step S102, the phase difference between the A-phase voltage and the B-phase voltage applied to the piezoelectric element 607 is set to +180° or −180°.

Note that FIG. 7 shows a case where the phase difference applied in the step S102 is set to −180°. Further, the phase difference between the A-phase voltage and the B-phase voltage in the step S102 is not required to be strictly ±180° insofar as it is possible to vibrate the movable unit 670 in the X-axis direction without practically moving the injection pipette 203 in the X-axis direction, and break the membrane of the transparent body 1001d without any trouble.

After confirming breakage of the membrane of the transparent body 1001d, the operator turns off the operation switch of the vibration mode M2 to stop the driving of the vibration element 660 in the vibration mode M2, and the process proceeds to a step S103. Note that breakage of the membrane of the transparent body 1001d can be confirmed by a video displayed on the display 4.

In the step S103, the operator operates the input unit 202 of the first manipulator 200 to drive the vibration element 660 in the movement mode M1 to thereby move the movable unit 670 in the negative direction of the X-axis, and separate the injection pipette 203 from the ovum 1001. In doing this, the phase difference between the A-phase voltage and the B-phase voltage is set to a plus value close to 0°, whereby it is possible to drive the injection pipette 203 (movable unit 670) in the negative direction of the X-axis at a very low speed. In a state after the step S103 has been terminated, the broken transparent body 1001dz has entered the injection pipette 203. Therefore, in a step S104, the operator operates the first injector device 300 to discharge the transparent body 1001dz from the injection pipette 203. Further, in the step S104, the operator operates the first injector device 300 to move the sperm 1004 to the tip end of the injection pipette 203.

Then, in a step S105, the operator drives the vibration element 660 in the movement mode M1 to move the movable unit 670 in the positive direction of the X-axis and press the injection pipette 203 into the ovum cell 1001a by a predetermined depth. In doing this, the phase difference between the A-phase voltage and the B-phase voltage is set to a minus value close to 0°, whereby it is possible to drive the injection pipette 203 (movable unit 670) in the positive direction of the X-axis at a very low speed. The AC phase difference c between the AC voltages, illustrated in the process from the step S104 to the step S105 is a very small phase difference, and hence it is illustrated in an exaggerated manner. After the injection pipette 203 has been thus pressed into the ovum cell 1001a, the operator turns on the operation switch of the vibration mode M2 to drive the vibration element 660 in the vibration mode M2 to thereby vibrate the vibration element 660 in the X-axis direction, and break the ovum cell membrane 1001b. In doing this, the phase difference between the A-phase voltage and the B-phase voltage applied to the piezoelectric element 607 is set to +180° or −180°. Note that FIG. 7 shows a case where the phase difference is set to −180°. Similar to the step S102, the phase difference between the A-phase voltage and the B-phase voltage in this step is not required to be strictly ±180° insofar as it is possible to break the ovum cell membrane 1001b without any trouble.

After confirming breakage of the ovum cell membrane 1001b, and turning off the operation switch of the vibration mode M2, in a step S106, the operator operates the first injector device 300 to inject the sperm 1004 into the ovum cell cytoplasm 1001c. In a step S107 after confirming injection of the sperm 1004 into the ovum cell cytoplasm 1001c, the operator operates the input unit 202 of the first manipulator 200 to drive the vibration element 660 in the movement mode M1 to thereby move the movable unit 670 in the negative direction of the X-axis. Thus, the injection pipette 203 is drawn out of the ovum 1001. In doing this, the phase difference between the A-phase voltage and the B-phase voltage is set to a plus value close to 0°, whereby it is possible to drive the injection pipette 203 (movable unit 670) in the negative direction of the X-axis at a very low speed. With this step S107, the series of the processing operations of the ICSI is terminated.

As described above, in the manipulator system 1 according to the present embodiment, it is possible to drive the vibration actuator 680 including the vibration element 660 in the movement mode M1 and the vibration mode M2. With this, it is possible to execute the piercing vibration and the translational driving of the injection pipette 203 by using the same actuator, and what is more, it is also possible to perform the very low-speed driving in the translational driving. Such configuration makes it possible to realize the stage device which is compact and is capable of performing the piercing vibration and the translational driving at a very low speed, at low costs.

In the present embodiment described above, the vibration actuator 680 is configured such that the vibration element 660 is fixed, and the contact body 604 is movable. However, inversely, it is also possible to configure the vibration actuator 680 such that the vibration element 660 is made movable, and is connected to the movable unit 670, and the contact body 604 is fixed.

According to the above-described embodiment, it is possible to perform the piercing vibration and the translational driving by using one actuator, and perform very low-speed driving in the translational driving with high accuracy.

In the above-mentioned conventional technique disclosed in pp. 91 to 93 of "Assisted Reproductive Technology Text" written by Yasuhisa Araki, published on January, 2015, by Ishiyaku Publishers, Inc., when the dial part 2005 of the injector device 2000 is manually operated, if the operation speed is low, the ovum cell membrane 1001b may not be broken. However, even if the operation speed of the dial part 2005 is too high, a delay occurs in the movement of the ovum cell membrane 1001b to be sucked into the injection pipette 1002, and the sucking operation is not stopped even after the operation of the dial part 2005 is stopped. Therefore, it is necessary to operate the dial part 2005 at a proper speed. Further, determination of whether or not the ovum cell membrane 1001b has been broken requires visual observation by an operator, for checking the movement of the ovum cell cytoplasm 1001c sucked into the injection pipette 1002. Further, unless the operator manually reverses the operation of the dial part 2005 immediately after the ovum cell membrane 1001b has been broken, too much of the ovum cell membrane 1001b is sucked into the injection pipette 1002. This may cause a problem that the broken ovum cell membrane 1001b prevents the sperm 1004 from being injected into the ovum cell cytoplasm 1001c.

From the above, the success rate of the ICSI depends on the determination performed by visual observation of an operator and the speed of the manual operation, and hence, the skilled technique is required.

Further, Japanese Laid-Open Patent Publication (Kokai) No. H08-290377 discloses a technique for performing an operation for sucking an ovum cell membrane and an operation for injecting a sperm by driving a diaphragm provided in an injection pipette using a piezoelectric element. An injector device, disclosed in Japanese Laid-Open Patent Publication (Kokai) No. H08-290377, is capable of performing the sucking operation and the injection operation by extending/compressing the piezoelectric element to drive the diaphragm provided in the injection pipette. However, there is a limit in the forward/backward movement amount of liquid in the injection pipette, which is caused by extension/compression of the piezoelectric element, and the determination of whether or not the ovum cell membrane has been broken requires a visual check.

To solve this problem, the following second to seventh embodiments each provide an injector device that enables an operator, who is less experienced in the membrane breaking operation, to easily perform desired processing with high accuracy, and a method of controlling the injector device.

Figure 9:
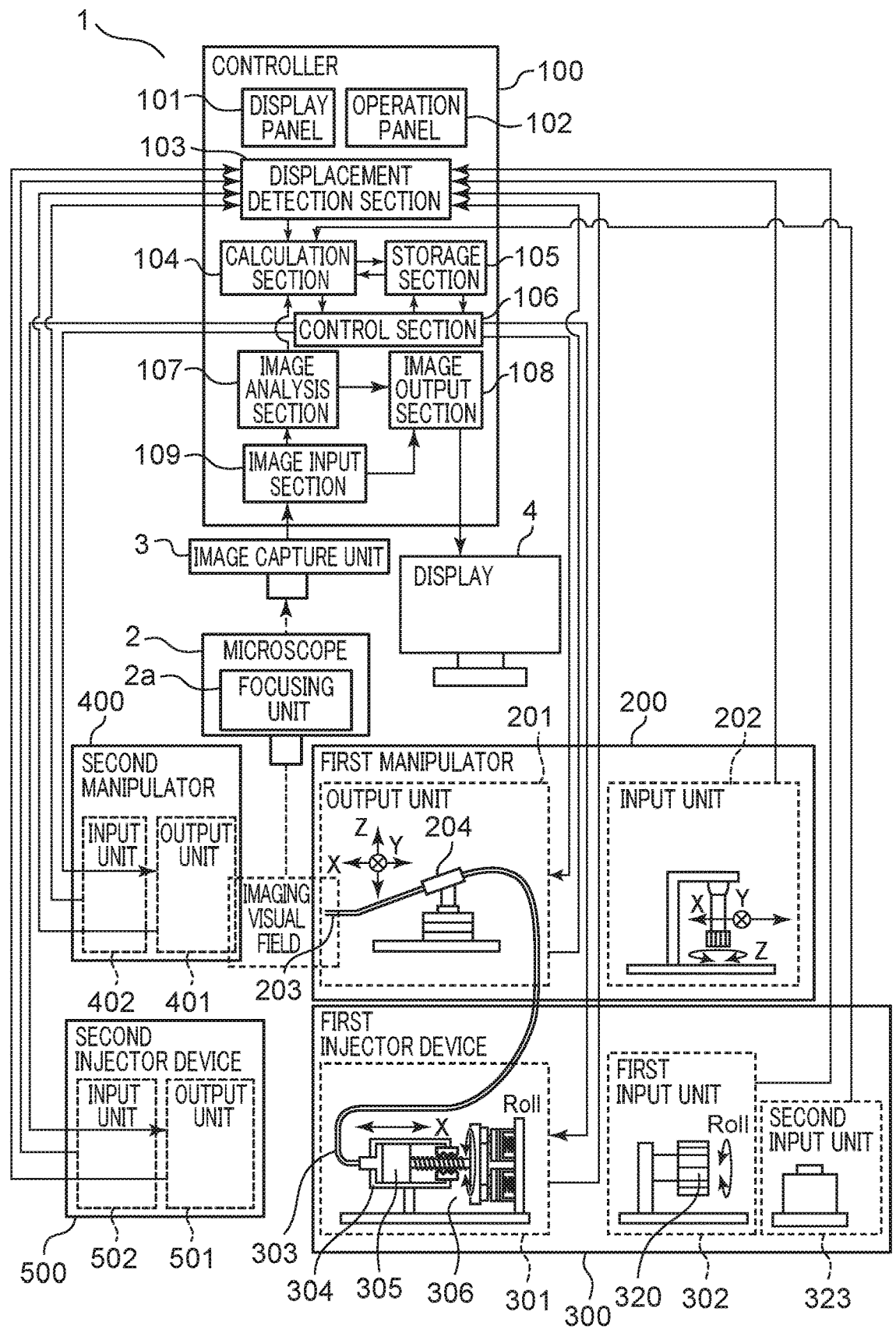
FIG. 9 is a block diagram useful in explaining the general configuration of a manipulator system according to a second embodiment.

FIG. 9 is a block diagram of the manipulator system 1 that performs the ICSI according to the second embodiment. Note that the same component elements as those of the above-described first embodiment are denoted by the same reference numerals, and description thereof is omitted.

The first injector device 300' includes an output unit 301 that operates a forward/backward movement amount L2 of the liquid 1005 in the injection pipette 203, and a first input unit 302 to which a value which continuously changes can be input.

Figure 10A:
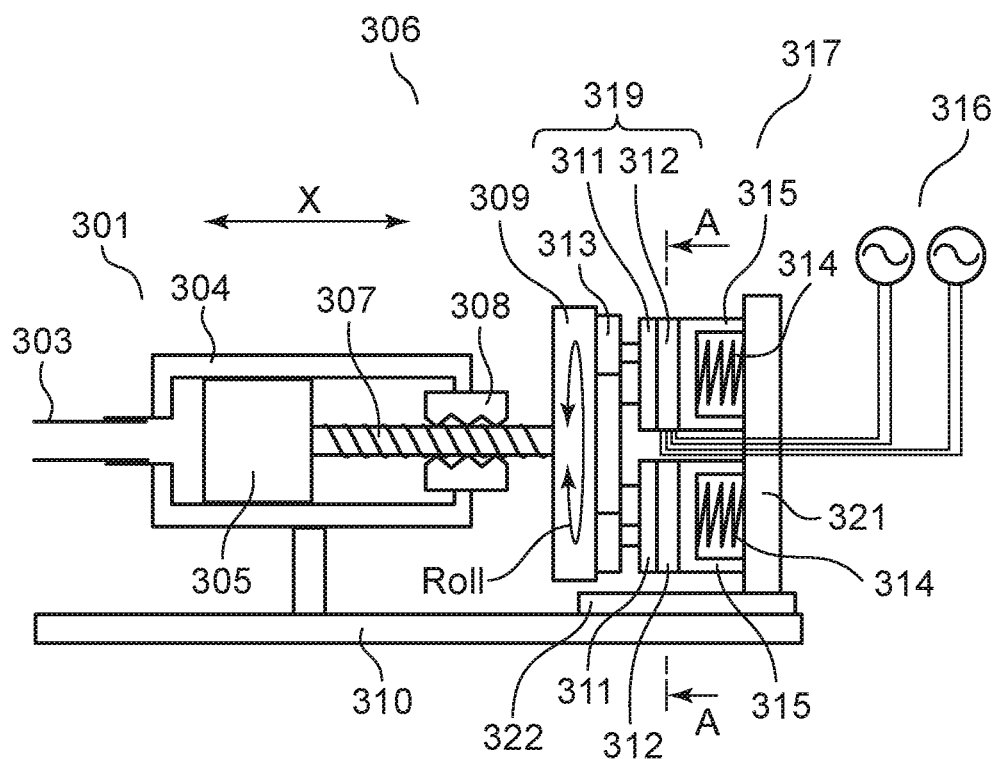
FIGS. 10A and 10B are cross-sectional views of an output unit of a first injector device.
Figure 10B:
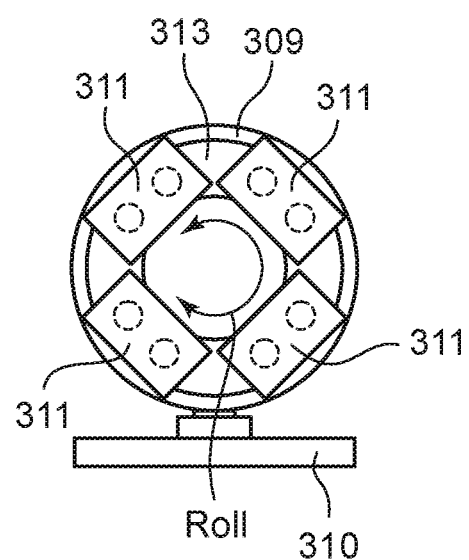

FIG. 10A is a cross-sectional view of the output unit 301 of the first injector device 300' of the second embodiment. FIG. 10B is a cross-sectional view taken along A-A in FIG. 10A.

The output unit 301 of the first injector device 300' includes the cylinder 304 to which the tube 303 can be connected, the piston 305 which can adjust the capacity by advancing and retreating in the cylinder 304, and a linear moving unit 306 which can drive the piston 305 to advance and retreat the same.

The tube 303 has one end connected to the cylinder 304, and the other end connected to the injection pipette 203 via the injection pipette holder 204 of the first manipulator 200.

The cylinder 304 is supported by a fixed member 310.

The linear moving unit 306 includes a female screw portion 308 formed in the cylinder 304, a male screw portion 307 formed on the shaft portion of the piston 305, a rotary member 309 provided at an end of the male screw portion 307 on a side opposite to the piston 305, and a vibration motor 317 which drives the rotary member 309.

The vibration motor 317 includes vibration elements 319 each having a vibration plate 311 and a piezoelectric element 312, and a friction member 313 which is brought into friction contact with the vibration elements 319. Further, the vibration motor 317 includes pressure members 314 each of which generate a pressure force for bringing the vibration element 319 associated therewith into friction contact with the friction member 313, and pressure force transmission members 315 each of which is disposed between the vibration element 319 and the pressure member 314 associated therewith, for transmitting a pressure force from the pressure member 314 to the vibration element 319.

The vibration motor 317 has the vibration elements 319 and the friction members 313 moved relative to each other in a relative movement direction by an elliptical motion, generated on the vibration elements 319 by applying two AC voltages 316, changeable in phase difference, to the piezoelectric elements 312.

The friction member 313 is provided on the rotary member 309.

The female screw portion 308 and the male screw portion 307 are engaged with each other, and hence when the rotary member 309 is rotated, the piston 305 advances/retreats relative to the cylinder 304. At this time, the rotary member 309 rotates about an axis of the female screw portion 308, and in the first injector device 300', this rotation direction is defined as the Roll direction, and the axial direction of the female screw portion 308 is defined as the X-axis direction.

The vibration motor 317 is supported by a supporting member 321. The supporting member 321 is held by a slide member 322 such that it is guidable in the X-axis direction. Further, the rotary member 309 is rotatably connected to the vibration motors 317 by a holding member, not shown. With this, even when the rotary member 309 is rotated to advance/retreat, the vibration motor 317 can advance/retreat without being separated from the rotary member 309.

With this arrangement, the vibration motor 317 rotates the rotary member 309, whereby the piston 305 can advance and retreat in the X-axis direction relative to the cylinder 304.

Although the first injector device 300', shown in FIGS. 10A and 10B, uses four vibration motors 317, the number of the vibration motors may be one, and is not limited to this example.

Further, the output unit 301 of the first injector device 300' has an encoder or the like, not shown, as a measuring section for detecting a rotational amount of the rotary member 309, and the measured rotational amount is detected by the displacement detection section 103 and is used for control of the output unit 301 of the first injector device. In doing this, the output unit 301 may include an encoder, not shown, for measuring not the rotational amount of the rotary member 309, but a linear movement amount of the cylinder 304, and in this case, the measured linear movement amount may be detected by the displacement detection section 103 and be used for control of the output unit 301 of the first injector device 300'.

The first injector device 300' includes the first input unit 302 to which a value which continuously changes can be input and a second input unit 323 to which binary signals can be input. The first input unit 302 of the first injector device 300' includes an operation section, such as a dial part 320, and a measurement section for measuring an operation amount of the dial part 320, such as an encoder, not shown. With this, the first injector device 300' can have the first input unit 302 to which the value which continuously changes can be input.

The measured operation amount is sent to the displacement detection section 103. Then, the operation amount sent to the displacement detection section 103 is sent to the output unit 301 of the first injector device 300' via the calculation section 104 and the control section 106. With this, the linear moving unit 306 can move the piston 305 by an amount corresponding to the operation amount input to the first input unit 302.

Note that although in the second embodiment, the first input unit 302 is configured such that the value which continuously changes can be input, as another example, the first input unit 302 may be one capable of multi-stage input with such a degree of resolution as will not cause a problem of performance.

A tube, not shown, is connected to the second injector device 500 and the holding pipette 403 of the second manipulator 400, whereby the second injector device 500 operates the inner pressure of the holding pipette 403.

Next, the operating modes of the first injector device 300' will be described.

The first injector device 300' has a first operating mode R1 in which the linear moving unit 306 move the piston 305 by an amount corresponding to a value input to the first input unit 302, and a second operating mode R2 in which the linear moving unit 306 stops the piston 305 regardless of a value input to the first input unit 302.

These modes are switched such that the first operating mode R1 is changed to the second operating mode R2 based on the result of analysis by the image analysis section. Further, when increase/decrease of a value input to the first input unit 302 is reversed in a state in which the first injector device 300' is in the second operating mode R2, the operating mode is switched to the first operating mode R1. Details of switching of these modes will be described hereinafter.

Figure 11:
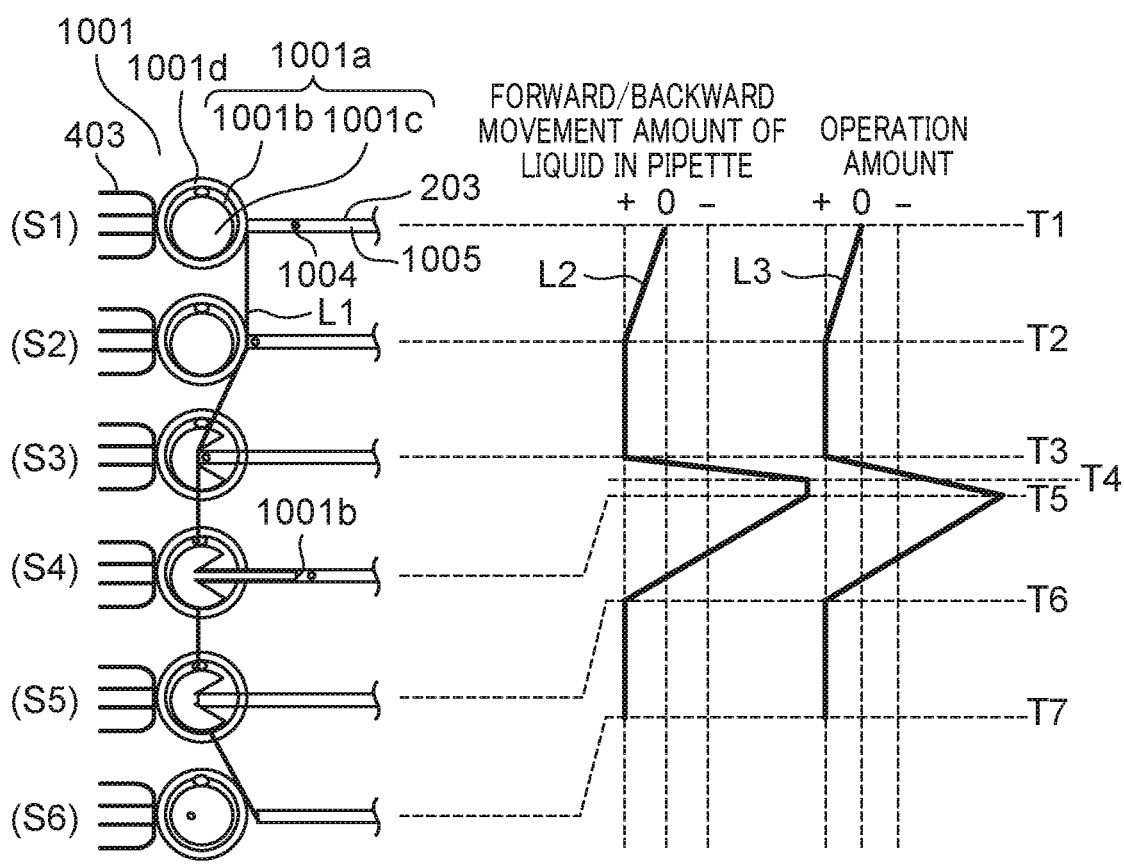
FIG. 11 is a diagram useful in explaining an operation procedure of ICSI using the manipulator system according to the second embodiment.

FIG. 11 shows the membrane breaking operation in the second embodiment. Steps S1 to S6 of a membrane breaking process will be described with reference to in FIG. 11. T1 to T7 each represent a time of each step. A solid line L1 indicates the position of the tip end point of the injection pipette 203. A solid line L2 indicates an amount of forward/backward movement of the liquid 1005 in the injection pipette 203, changed by movement of the piston 305 by the linear moving unit 306, and a solid line L3 indicates the operation amount of the first input unit 302 of the first injector device 300'.

In this process, the movement amount of the sperm 1004, the movement amount of the ovum cell membrane 1001b, and the movement amount of the ovum cell cytoplasm 1001c are collectively referred to as the forward/backward movement amount L2 of the liquid 1005. The sign of the forward/backward movement amount L2 of the liquid 1005 is plus when the liquid 1005 advances toward the ovum 1001. The sign of the operation amount L3 of the first injector device 300' is plus when the dial part 320 is operated to advance the liquid 1005 in the plus direction, i.e. toward the ovum 1001.

First, in a step S1 in FIG. 11, the sperm 1004 is sucked into the injection pipette 203 with the liquid 1005, such as polyvinylpyrrolidone (PVP) solution for making it easy to operate the sperm. Then, the injection pipette 203 having sucked the sperm 1004 therein is moved close to the ovum 1001 held by the holding pipette 403 (T1).

Next, in a step S2 in FIG. 11, the operator operates the dial part 320 of the first injector device 300' in the plus direction to move the sperm 1004 together with the liquid 1005 in the plus direction according to the operation amount L3 of the dial part 320, and move the sperm 1004 to a point close to the tip end point of the injection pipette 203 (T2).

In the operation from the time T1 to the time T2, the first injector device 300' operates in the first operating mode R1 in which the linear moving unit 306 moves the piston 305 to move the liquid 1005 forward/backward by an amount corresponding to the operation amount L2 of the dial part 320.

After the sperm 1004 has been moved, in a step S3 in FIG. 11, the operator operates the first manipulator 200 to press the injection pipette 203 into the ovum cell 1001a to an illustrated degree (T3). At this time, the transparent body 1001d around the ovum cell 1001a is broken by the injection pipette 203.

Then, when the process proceeds from the step S3 to a step S4 in FIG. 11, the operator operates the dial part 320 of the first injector device 300' in the minus direction (from T3 to T5).

With this, the ovum cell membrane 1001b is sucked into the injection pipette 203, and it is possible to break the ovum cell membrane 100b. Assuming that the time at which the ovum cell membrane 1001b is broken is indicated by T4, in the operation from the time T3 to the time T4, the first injector device 300' operates in the first operating mode R1 in which the linear moving unit 306 moves the piston 305 to move the liquid 1005 forward/backward by an amount corresponding to the operation amount L2 of the dial part 320. In the operation from the time T4 to the time T5, the first injector device 300' operates in the second operating mode R2 in which although the dial part 320 is operated, the linear moving unit 306 at rest, and the liquid 1005 is not moved forward/backward. At the time T4, when it is determined by the image analysis section 107 that a change in a predetermined portion of the image acquired by the image capture section 3 has exceeded a predetermined threshold value, the operating mode is automatically switched from the first operating mode R1 to the second operating mode R2.

The change in the predetermined portion of the image, checked by the image analysis section 107 for the determination, may be a change in the flow rate of the liquid in the injection pipette 203, for example. The liquid in the injection pipette 203 is formed by the ovum cell cytoplasm 1001c, a PVP solution, and so forth, and breakage of the ovum cell membrane 1001b causes a change in the flow rate of a fluid, such as the ovum cell cytoplasm 1001c and the PVP solution, and hence it is possible to use the change in flow rate for the determination performed by the image analysis section 107.

Further, as another example of the change in predetermined portion of the image is a change in the speed of the sperm 1004 or a change in the shape of the ovum cell membrane 1001b.

A time period from T3 to T5 is a short time, compared with the time periods of the other operations. This is because unless the liquid 1005 is moved forward/backward at a proper speed, the ovum cell membrane 1001b cannot be broken. At this time, in the conventional embodiment in which the ovum cell membrane 1001b is visually checked by an operator to perform the above determination, the operation is continued so long as the person is determining whether or not the membrane has been broken, the liquid 1005 continues to retreat in the minus direction, so that too much of the ovum cell membrane 1001b is sucked. As a result, the ovum cell membrane 1001b prevents the sperm 1004 from being injected into the ovum 1001.

To prevent this, according to the second embodiment, the image analysis section 107 determines that the ovum cell membrane 1001b has been broken at the time T4, and the operating mode is automatically switched to the second operating mode R2. Therefore, in the operation from the time T4 to T5, even when the dial part 320 is operated, the linear moving unit 306 is stopped to prevent the liquid 1005 from being moved forward/backward, so that too much of the ovum cell membrane 1001b is not sucked. Therefore, it is possible to perform the membrane breaking operation without requiring a skilled technique dependent on the visual determination and operation skill of an operator.

Next, the operation for injecting the sperm 1004 in the step S4 in FIG. 11 will be described.

Breakage of the ovum cell membrane 1001b can be confirmed not only by observing the stop or delay of motion of the ovum cell cytoplasm 1001c, but also by confirming that the operating mode is the second operating mode R2. The second operating mode R2 is displayed on the display 4 or the display panel 101.

When breakage of the ovum cell membrane 1001b has been confirmed, the operator operates the dial part 320 in the plus direction to inject the sperm 1004 into the ovum 1001 (T5). At this time (T5), since the operation amount L3 of the dial part 320 is reversed from the minus direction to the plus direction, the operating mode is automatically switched from the second operating mode R2 to the first operating mode R1. Then, the linear moving unit 306, which has been stopped, is enabled to move the piston 305 according to the operation amount of the dial part 320, and the liquid 1005 can advance in the plus direction.

In a step S5 in FIG. 11, when it is confirmed that the sperm 1004 has entered the ovum cell cytoplasm 1001c, the operator stops the operation of the dial part 320 (T6).

In a step S6 in FIG. 11, the operator operates the first manipulator 200 to draw the injection pipette 203 out of the ovum 1001 (T7).

From the above, according to the second embodiment, it is possible to provide the injector device that makes it possible to perform the membrane breaking operation without requiring a skilled technique dependent on the visual determination and operation skill of an operator.

Figure 12A:
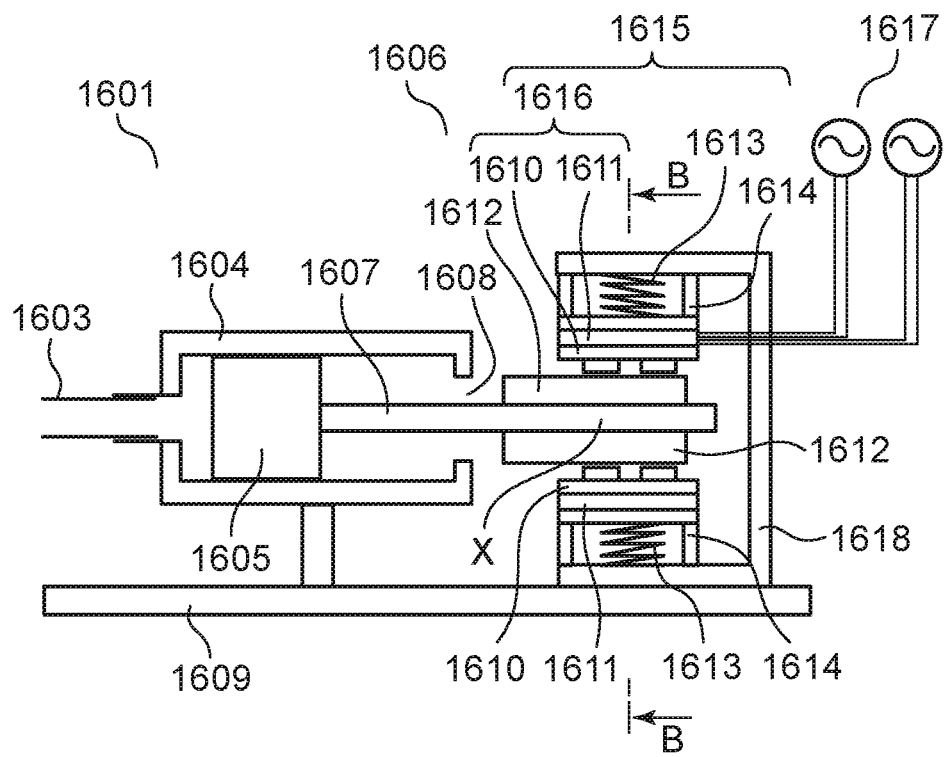
FIGS. 12A and 12B are cross-sectional views of another form of the output unit of the injector device.
Figure 12B:
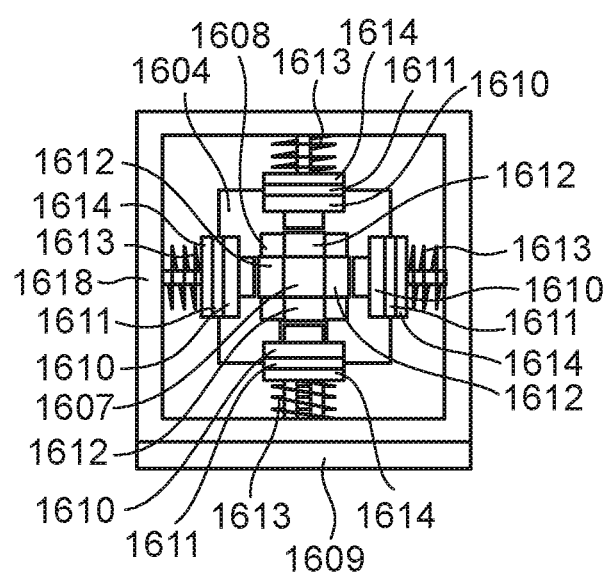

Next, an output section 1601 of the injector device as another form of the output unit 301 of the injector device, used in the second embodiment, will be described with reference to FIGS. 12A and 12B. FIG. 12A is a cross-sectional view of the output section 1601 of the injector device. FIG. 12B is a cross-sectional view taken along B-B in FIG. 12A.

The output section 1601 of the injector device includes a cylinder 1604 to which a tube 1603 can be connected, a piston 1605 which can adjust the capacity by advancing and retreating in the cylinder 1604, and a linear moving unit 1606 which can drive the piston 1605 to advance and retreat the same.

The tube 1603 has one end connected to the cylinder 1604 and the other end connected to the injection pipette 203 via the injection pipette holder 204 of the first manipulator 200. The cylinder 1604 is supported by a fixed member 1609.

The linear moving unit 1606 includes a shaft portion 1607 communicating with an opening 1608 formed in the cylinder 1604, and a vibration motor 1615 provided on the shaft portion 1607.

The vibration motor 1615 includes vibration elements 1616 each having a vibration plate 1610 and a piezoelectric element 1611, and friction members 1612 each of which is brought into friction contact with the vibration element 1616 associated therewith. Further, the vibration motor 1615 includes pressure members 1613 each of which generates a pressure force for bringing the vibration element 1616 associated therewith into friction contact with the friction member 1612 associated therewith, and pressure force transmission members 1614 each of which is disposed between the vibration element 1616 and the pressure member 1613 associated with, and transmits a pressure force from the pressure member 1613 to the vibration element 1616. Further, the vibration motor 1615 are held by a casing member 1618 supported by the fixed member 1609.

The vibration motor 1615 has the vibration elements 1616 and the friction members 1612 moved relative to each other in a relative movement direction by an elliptical motion, generated on the vibration elements 1616 by applying two AC voltages 1617, changeable in phase difference, to the piezoelectric elements 1611. Details of this mechanism is described e.g. in Japanese Laid-Open Patent Publication (Kokai) No. 2012-116107, and hence description thereof is omitted.

With this arrangement, the piston 1605 is enabled to advance and retreat in the X-axis direction indicated by "X" in FIG. 12A by the linear moving unit 1606 including the vibration motor 1615, and it is possible to operate the forward/backward movement amount of the liquid 1005 in the injection pipette 203 connected to the tube 1603.

Although the second embodiment employs the linear moving unit including one of the vibration motors described with reference to FIGS. 10A and 10B and FIGS. 12C and 12D, this is not limitative, but there may be employed a linear moving unit including a stepping motor, a voice coil motor, or the like.

From the above, according to the second embodiment, it is possible to provide the injector device that makes it possible to perform the membrane breaking operation without requiring a skilled technique dependent on the visual determination and operation skill of an operator. This enables even an operator who is less experienced in the membrane breaking operation to easily perform desired processing with high accuracy.

Next, a third embodiment will be described. In the second embodiment, switching of the operating mode from the second operating mode R2 to the first operating mode R1 can be performed by reversing the increase/decrease of the operation amount of the dial part. In the third embodiment, another method of switching the operating mode will be described. A manipulator system that performs ICSI according to the third embodiment is the same as that of the second embodiment, and hence description thereof is omitted.

First, the operation panel 102 is provided with a switch section, not shown.

The method of switching the operating mode according to the third embodiment makes it possible to switch the operating mode to the first operating mode, by operating the switch section in a state in which the injector device is in the second operating mode.

Figure 13:
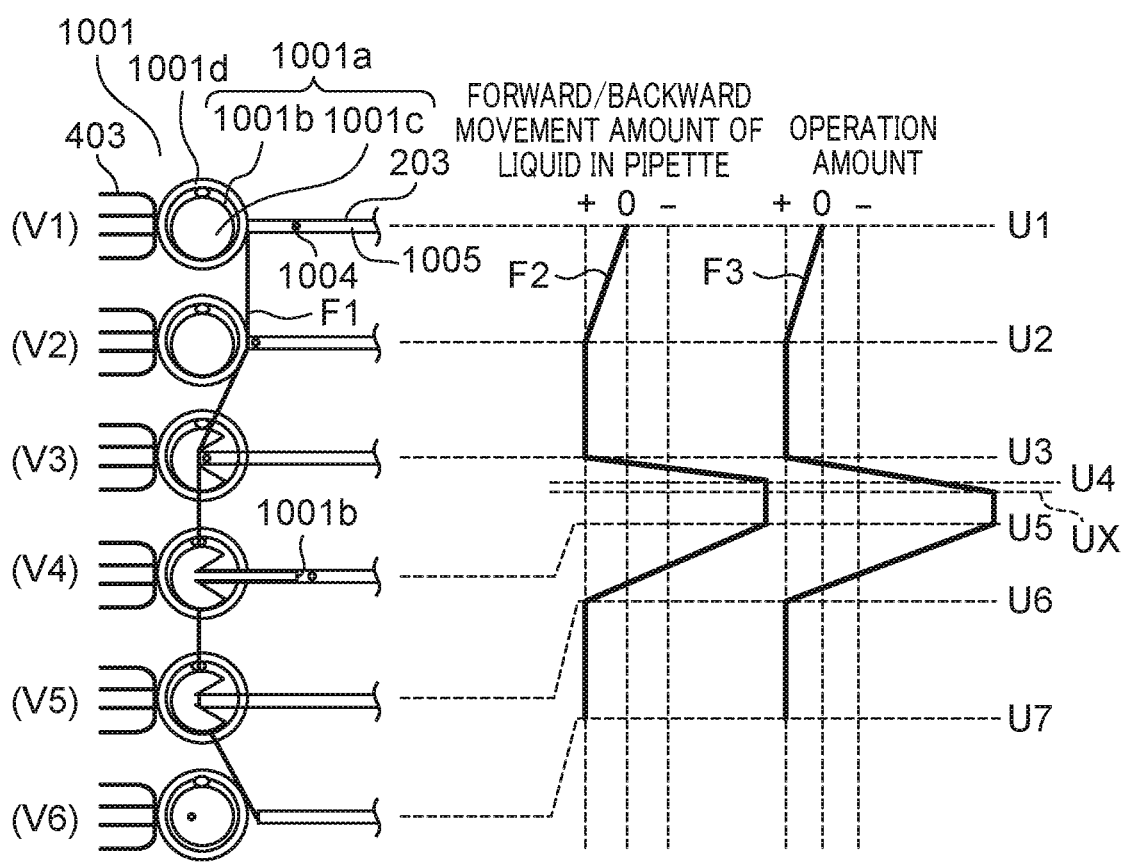
FIG. 13 is a diagram useful in explaining an operation procedure of an ovum cell membrane breaking operation in a third embodiment.
Figure 14A:
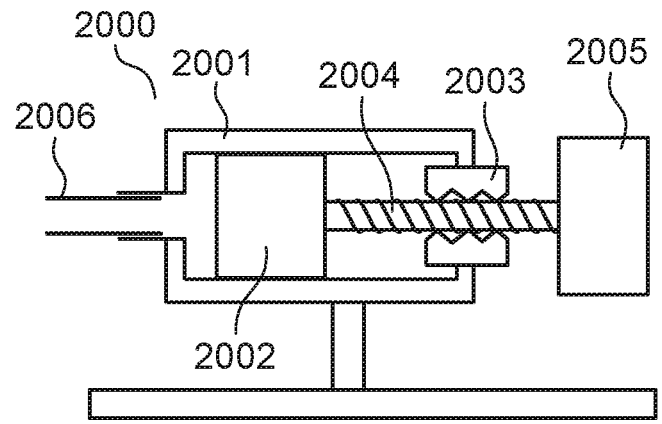
FIGS. 14A and 14B are a cross-sectional view of a conventional injector device, and a diagram useful in explaining the ovum cell membrane breaking operation performed by the conventional injector device, respectively.
Figure 14B:
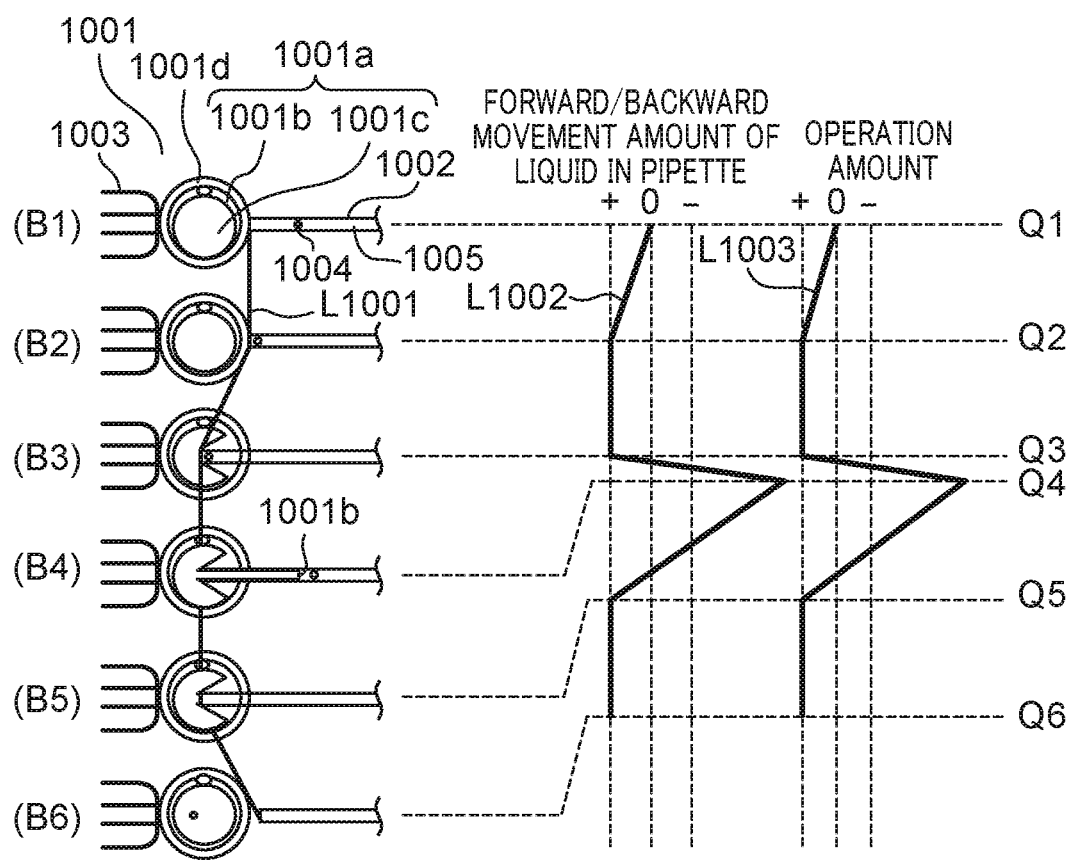

FIG. 13 shows the membrane breaking operation in the third embodiment.

A position F1 of the tip end point of the injection pipette 203 from a step V1 to a step V6 in FIG. 13 is the same as the position L1 of the tip end point of the injection pipette 203 from the step S1 to the step S6 in FIG. 11 in the second embodiment. A forward/backward movement amount F2 of the liquid 1005 in the injection pipette 203 is the same as the forward/backward movement amount L2 of the liquid 1005 in the injection pipette 203 in FIG. 11. Further, an operation amount F3 of the dial part 320 in a time period from a time U1 to a time UX in FIG. 13, in which the ovum cell membrane 1001b is broken, the operating mode is switched, and breakage of the membrane is confirmed e.g. on the operation panel, is also the same as the operation amount L3 of the dial part 320 in the time period from the time T1 to the time T5 in FIG. 11.

In the second embodiment, at the time T5, the increase/decrease of the input value of the dial part 320 is reversed from the minus direction to the plus direction to switch the operating mode, whereby the operation is shifted to the operation for injecting the sperm 1004. In the third embodiment, after confirming breakage of the membrane at the time UX, the switch section provided on the operation panel is pressed at a time U5 to switch the operating mode from the second operating mode R2 to the first operating mode R1. By performing the operation for pressing the switch section, a time period during which the dial part 320 is not operated is generated after confirming breakage of the membrane (UX) until the switch section is pressed (U5).

The operation for injecting the sperm 1004 after switching the operating mode, performed from the time U5 to a time U7 in FIG. 13, is the same as the injection operation performed from the time T5 to the time T7 in FIG. 11.

Although the switch section is provided on the operation panel 102, the switch section may be a foot pedal, not shown. Further, a touch panel system formed by integrating the display panel 101 and the operation panel 102 may be employed. Further, the switch section may be arranged on the injector device.

From the above, according to the third embodiment, similar to the second embodiment, it is possible to provide the injector device that makes it possible to perform the membrane breaking operation without requiring a skilled technique dependent on the visual determination and operation skill of an operator.

Next, a fourth embodiment will be described. A manipulator system that performs ICSI according to the fourth embodiment is the same as that of the second embodiment, and hence description thereof is omitted.

Note that although in the fourth embodiment, the first input unit 302 is configured such that the value which continuously changes can be input, as another example, the first input unit 302 may be one capable of multi-stage input with such a degree of resolution as will not cause a problem of performance.

The second input unit 323 of the first injector device uses e.g. a toggle switch performing alternate operation, serving as an input unit to which binary signals of on and off can be input. One of the on and off signals is sent to the calculation section 104, and is used for control of the operation mode of the first injector device 300', described hereinafter.

The second manipulator 400 has the same configuration as that of the first manipulator 200, and hence illustration thereof is omitted. However, differently from the first manipulator 200, the second manipulator 400 includes not the injection pipette 203, but the holding pipette 403 appearing in FIG. 15.

The second injector device 500 has the same configuration as that of the first injector device 300', and hence illustration thereof is omitted. However, differently from the first injector device 300', a tube (not shown) is connected between the second injector device 500 and the holding pipette 403 of the second manipulator 400, whereby the second injector device 500 operates inner pressure of the holding pipette 403.

Next, the operation mode of the first injector device 300' will be described.

The first injector device 300' has a first operation mode H1 in which the linear moving unit 306 moves the piston 305 by an amount corresponding to a value input to the first input unit 302. Further, the first injector device 300' has a second operation mode H2 in which when a predetermined signal is input to the second input unit 323, the linear moving unit 306 causes the piston 305 to linearly advance and stop according to a predetermined sequence. The predetermined signal refers e.g. to a signal indicating detection that the switch of the second input unit 323 been pressed. Details of the operation will be described with reference to FIG. 15.

Figure 15:
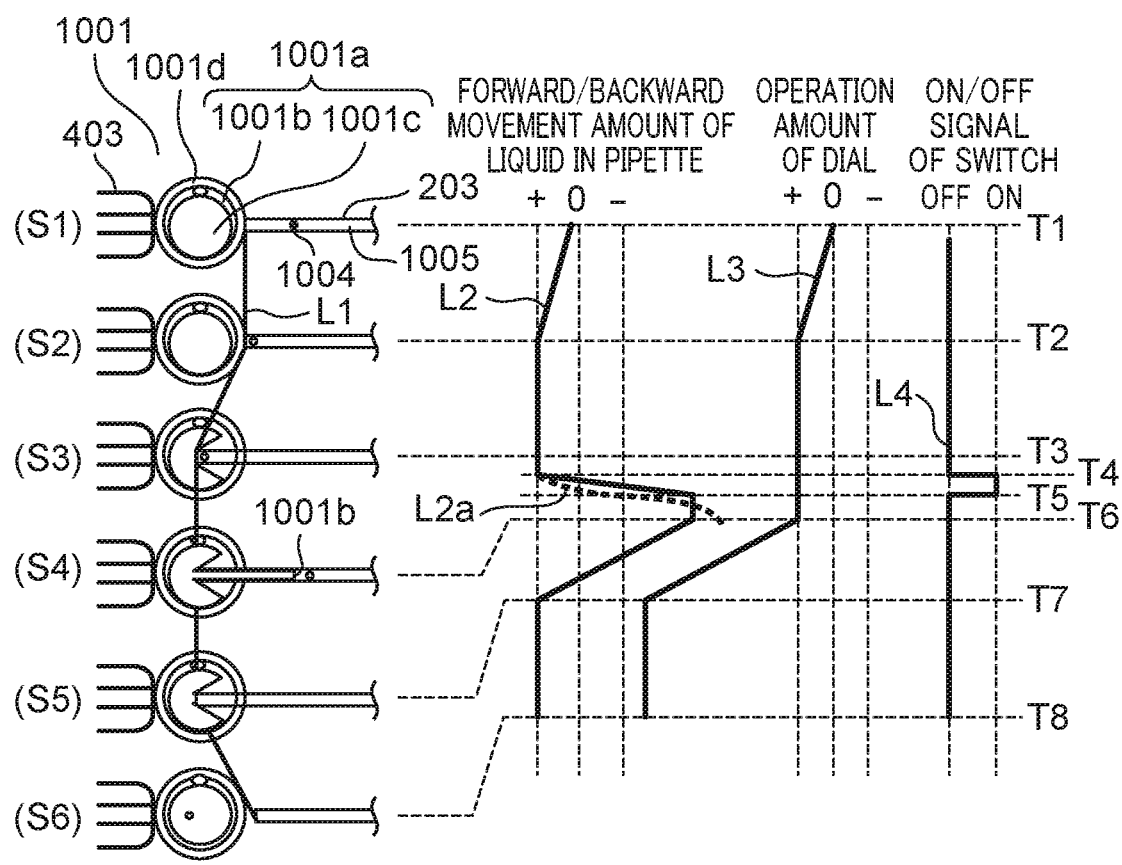
FIG. 15 is a diagram useful in explaining an operation procedure of an ovum cell membrane breaking operation in a fourth embodiment.

FIG. 15 shows the membrane breaking operation in the fourth embodiment. The operation process for breaking the membrane will be described according to steps S1 to S6 in FIG. 15. T1 to T8 represent a time of each step. A solid line L1 indicates the position of the tip end point of the injection pipette 203. A solid line L2 indicates an amount of forward/backward movement of the liquid 1005 in the injection pipette 203, changed by movement of the piston 305 by the linear moving unit 306. A solid line L3 indicates the operation amount of the first input unit 302 of the first injector device 300'. Further, a solid line L4 indicates an on/off-signal input to the switch of the second input unit 323.

The forward/backward movement amount L2 of the liquid 1005 refers to movement of the liquid in the injection pipette 203, which is the same as the movement of the sperm 1004 floating in the liquid.

The sign of the forward/backward movement amount L2 of the liquid 1005 is plus when the liquid 1005 advances toward the ovum 1001. The sign of the operation amount L3 of the first injector device 300' is plus when the dial part 320 is operated to advance the liquid 1005 in the plus direction, i.e. toward the ovum 1001.

First, in a step S1 in FIG. 15, the sperm 1004 is sucked into the injection pipette 203 together with the liquid 1005, such as polyvinylpyrrolidone (PVP) solution, for making it easy to operate the sperm 1004. Then, the injection pipette 203 having sucked the sperm 1004 therein is moved close to the ovum 1001 held by the holding pipette 403 (T1).

Next, in a step S2 in FIG. 15, the operator operates the dial part 320 of the first injector device 300' in the plus direction. Then, the operator moves the sperm 1004 in the plus direction together with the liquid 1005 according to the operation amount L3 of the dial part 320 to thereby move the sperm 1004 close to the vicinity of the tip end point of the injection pipette 203 (T2).

In the operation from the time T1 to the time T2, the first injector device 300' operates in the first operating mode H1 in which the linear moving unit 306 moves the piston 305 to move the liquid 1005 forward/backward by an amount corresponding to the operation amount L2 of the dial part 320.

After the sperm 1004 has been moved, in a step S3 in FIG. 15, the operator operates the first manipulator 200 to press the injection pipette 203 into the ovum cell 1001a to an illustrated degree (from T2 to T3). At this time, the transparent body 1001d around the ovum cell 1001a is broken by the injection pipette 203.

Then, the second operation mode H2 in the operation from the time T3 (S3) to the time T6 (S4) in FIG. 15 will be described.

When the injection pipette 203 has been pressed into the ovum cell 1001a, the operation is shifted from the operation of the first manipulator 200 to the operation of the second input unit 323 (from T3 to T4). Then, the operator changes the switch of the second input unit 323 from off to on (T4). Then, the on-signal is sent from the second input unit 323 to the calculation section 104, and is output to the output unit 301 via the control section 106 as the drive amount. This drive amount is specified such that the linear moving unit 306 drives the piston 305 at a predetermined acceleration to enable the same to move the liquid 1005 forward/backward at a proper speed.

The linear moving unit 306 of the output unit 301 having received the command of the drive amount drives the piston 305 at the predetermined acceleration to move the liquid 1005 forward/backward at the proper speed, and cause the ovum cell membrane 100b to be sucked into the injection pipette 203 (from T4 to T5).

After confirming breakage of the sucked ovum cell membrane 1001b, the operator turns off the switch of the second input unit 323 (T5). As a result, the linear moving unit 306 is stopped, and the forward/backward movement of the liquid 1005 is accordingly stopped.

An operation mode, described above, in which when the on signal is manually input to the second input unit 323, the linear moving unit 306 drives the piston at a predetermined acceleration, and when the off signal is manually input to the second input unit 323, the linear moving unit 306 is immediately stopped is referred to as the second operation mode H2.

A time period from the time T4 to the time T5, in which the ovum cell membrane 1001b is being sucked, is a short time, compared with the time periods of the other operations. This is because it is necessary to move the liquid 1005 forward/backward at a proper speed at which the ovum cell membrane 1001b can be easily broken. A broken line L2a in FIG. 15 indicates the forward/backward movement amount of the liquid 1005 in a case where the dial part 320 of the first input unit 302 is manually operated. In the case of the manual operation, when the liquid 1005 has started to be moved forward/backward at the time T4, the linear moving speed of the liquid 1005 is low and unstable, and when stopping the movement, a delay is caused in action of stopping the dial part 320.

Therefore, according to the fourth embodiment, when starting the driving, the linear moving unit 306 drives the piston 305 at a stable acceleration to move the liquid 1005 forward/backward at a proper speed. Further, when stopping the driving, it is possible to rapidly stop the driving. Therefore, compared with the case of the manual operation, it is possible to perform the membrane breaking operation without requiring a skilled technique dependent on the operation skill.

Next, the operation for injecting the sperm 1004 in a step S4 in FIG. 15 will be described.

After confirming breakage of the ovum cell membrane 1001b, to inject the sperm 1004 into the ovum 1001, the operator operates the first input unit 302 to move the liquid 1005 forward/backward (T6). Injection of the sperm 1004 is performed in the first operation mode H1 for moving the liquid 1005 by an amount corresponding to a value input to the first input unit 302.

Then, in a step T5 in FIG. 15, when it is confirmed that the sperm 1004 has entered the ovum cell cytoplasm 1001c, the operator stops the operation of the first input unit 302 (T7).

Finally, in a step S6 in FIG. 15, the operator operates the first manipulator 200 to draw the injection pipette 203 out of the ovum 1001 (T8).

As described above, according to the fourth embodiment, it is possible to provide the injector device that makes it possible to perform the membrane breaking operation without requiring a skilled technique dependent on the visual determination and operation skill of an operator. This enables even an operator who is less experienced in the membrane breaking operation to easily perform desired processing with high accuracy.

Figure 16:
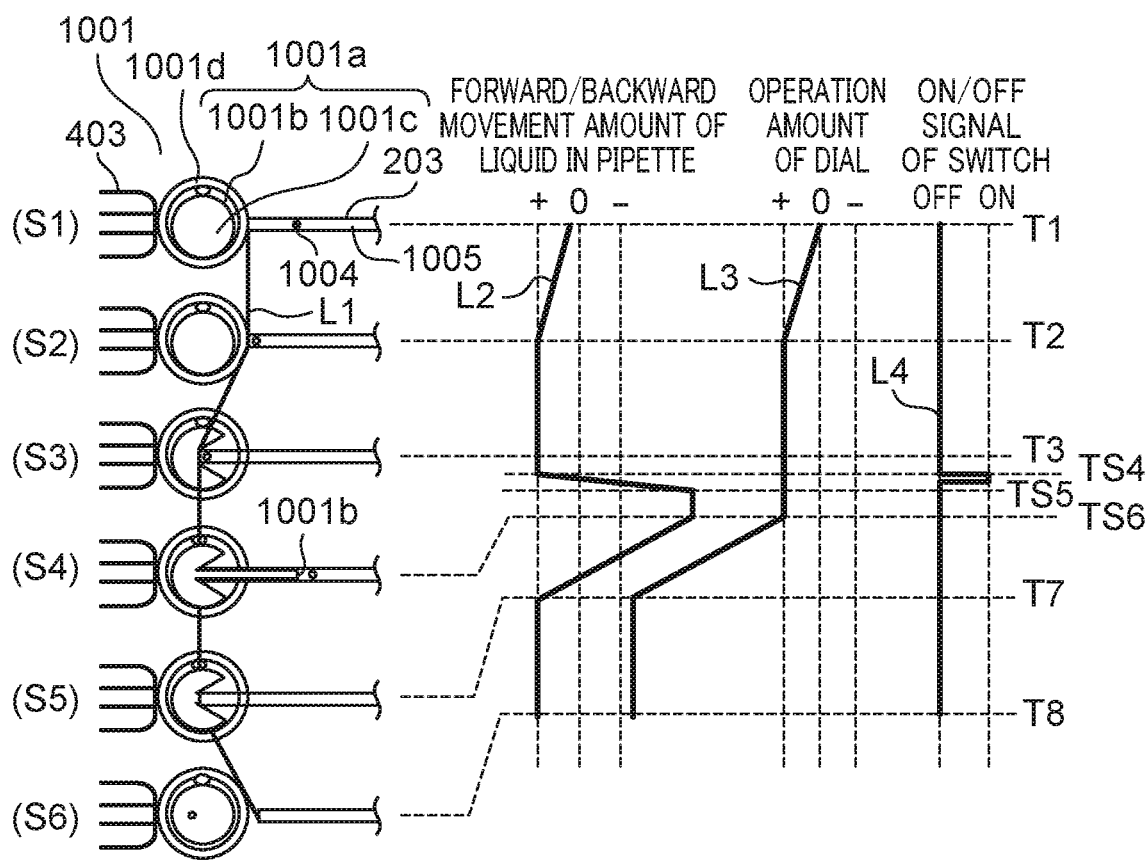
FIG. 16 is a diagram useful in explaining an operation procedure of an ovum cell membrane breaking operation in a fifth embodiment.

Next, a fifth embodiment will be described. In the fourth embodiment, the second operation mode H2, in which the linear moving unit 306 drives the piston 305 at the predetermined acceleration when the on-signal is manually input to the second input unit 323 and stops when the off-signal is manually input, has been described. In the fifth embodiment, a description will be given of the membrane breaking operation using a second operation mode J2 as another form of the second operation mode. FIG. 16 shows the membrane breaking operation using the fifth embodiment. Description of the same steps in FIG. 16 as those in FIG. 15 is omitted.

In a step S3 in FIG. 16, the injection pipette 203 is pressed into the ovum cell 1001a (T3). Then, the operator operates the switch of the second input unit 323 (TS4). The switch used in the fifth embodiment uses e.g. a tact switch which performs a momentary operation, in which the switch is turned on while the switch is being pressed, and turned off when the hand is removed from the switch.

When the operator presses the switch of the second input unit 323, the linear moving unit 306 is driven at a predetermined acceleration to suck the ovum cell membrane 1001b into the injection pipette 203 at a proper speed, and break the same (from TS4 to TS5). After that, when the forward/backward movement amount of the liquid 1005 reaches a predetermined amount, the linear moving unit 306 automatically stops (TS5). The predetermined acceleration is set, by determining in advance a proper speed at which the membrane is easily broken, such that the determined proper speed is realized by the predetermined acceleration. Further, the predetermined forward/backward movement amount is determined and set in advance so as to prevent the ovum cell membrane 1001b from being excessively sucked after breaking the membrane.

After confirming breakage of the ovum cell membrane 1001b at the time TS5, the operator operates the first input unit 302 to shift the operation to the operation for injecting the sperm 1004 (TS6).

As described above, the second operation mode J2 refers to an operation mode in which the switch of the second input unit 323 pressed to cause the linear moving unit 306 to drive the piston 305 at a predetermined acceleration, and automatically stop when the liquid 1005 is moved forward/backward by a predetermined movement amount at a proper speed.

Therefore, although in the fourth embodiment, only the start of the driving of the linear movement is automatically performed, and the stop of the driving depends on visual confirmation, in the fifth embodiment, it is possible to start and stop the driving of the linear movement according to a predetermined sequence by using the second operation mode J2. Therefore, the fifth embodiment is more advantageous than the fourth embodiment in the effect that the injector device makes it possible to perform the membrane breaking operation without requiring a skilled technique dependent on visual determination and operation skill of performed of an operator. This enables an operator who is less experienced in the membrane breaking operation to easily perform desired processing with high accuracy.

Next, a sixth embodiment will be described. In the fourth embodiment, the description has been given of the second operation mode H2 in which the linear moving unit 306 drives the piston 305 at the predetermined acceleration to move the liquid 1005 at the proper speed when the on-signal is manually input to the second input unit 323, and stops when the off-signal is manually input. In the fifth embodiment, the description has been given of the second operation mode J2 in which the linear moving unit 306 drives the piston 305 at the predetermined acceleration when the on-signal is manually input to the second input unit 323, and automatically stops when the liquid 1005 is moved forward/backward by the predetermined movement amount at the proper speed.

In the sixth embodiment, a description will be given of a second operation mode K2 with reference to FIG. 16, in which when it is determined by the image analysis section 107 that the moving speed of a predetermined portion (object) of an image acquired by the image capture section 3 has exceeded a predetermined threshold value in the second operation mode, the linear moving unit 306 automatically stops.

In the sixth embodiment, for example, similar to the fifth embodiment, a tact switch is used which is turned on while the switch is being pressed and turned off when the hand is removed from the switch.

Similar to the fifth embodiment (from TS4 to TS5), when the operator presses the switch of the second input unit 323, the linear moving unit 306 drives the piston 305 at a predetermined acceleration to suck the ovum cell membrane 1001b into the injection pipette 203. At this time, the image capture section 3 has acquired an image, and when it is determined by the image analysis section 107 that the moving speed of a predetermined portion of the acquired image has exceeded the predetermined threshold value, the linear moving unit 306 automatically stops and the forward/backward movement of the liquid 1005 is also stopped (TS5).

The change in the predetermined portion of the image, checked by the image analysis section 107 for the determination, may be a change in the flow rate of the liquid in the injection pipette 203, for example. The liquid in the injection pipette 203 is formed by the ovum cell cytoplasm 1001c, a PVP solution, and so forth, and breakage of the ovum cell membrane 1001b causes a change in the flow rate of a fluid, such as the ovum cell cytoplasm 1001c and the PVP solution, and hence it is possible to use the change in flow rate for the determination performed by the image analysis section 107.

Further, as another example of the change in predetermined portion of the image is a change in the speed of the sperm 1004 or a change in the shape of the ovum cell membrane 1001b.

After confirming breakage of the ovum cell membrane 1001b at the time TS5, the operator operates the first input unit 302 to shift the operation to the operation for injecting the sperm 1004 (TS6).

As described above, the second operation mode K2 refers to an operation mode in which the linear moving unit 306 is driven at a predetermined acceleration when the on-signal is manually input to the second input unit 323, and stops when it is determined by the image analysis section 107 that the moving speed of a predetermined portion of an acquired image has exceeded a predetermined threshold value.

Therefore, although the fourth embodiment employs the operation mode in which the driving is stopped by visual determination and the fifth embodiment employs the operation mode in which the driving is stopped when the forward/backward movement amount of the liquid reaches a predetermined amount, the sixth embodiment uses the second operation mode K2, whereby it is possible to stop the driving when breakage of the ovum cell membrane is determined by the image analysis section 107. Therefore, the sixth embodiment is more advantageous than the fifth embodiment in the effect that the injector device makes it possible to perform the membrane breaking operation without requiring a skilled technique dependent on visual determination and operation skill of performed of an operator. This enables an operator who is less experienced in the membrane breaking operation to easily perform desired processing with high accuracy.

Next, a seventh embodiment will be described. Although in the fourth to six embodiments, the second input unit 323 is provided in the first injector device 300', the switch of the second input unit 323 may be provided in the first input unit 302, and further alternatively, the second input unit 323 may be provided in the operation panel 102. Further, a foot pedal, not shown, may be provided, and operated as the second input unit 323.

However, if the foot pedal is provided as the second input unit 323, an operator is capable of operating the foot pedal by a foot while manually operating the first input unit 302. As a result, there is a possibility that the operation amount of the first input unit 302 and a signal from the second input unit 323 are simultaneously input to the controller 100. That is, the driving in the first operation mode H1 and the driving in the second operation mode H2, J2, or K2 can be performed at the same time.

To prevent this, in the seventh embodiment, a switching unit for switching an input section to receive the input between the first input unit 302 and the second input unit 323 is provided.

As the switching unit, a switch capable of inputting a binary signal, such as a toggle switch that performs an alternate operation, not shown, is provided in the operation panel 102, the first input unit 302, or the like.

The membrane breaking method using the switching unit will be described with reference to FIG. 17. Description of the same steps in FIG. 17 as those in FIG. 15 is omitted. Part of L3 in FIG. 17, indicated by a broken line, indicates that even when the dial part 320 of the first input unit 302 is operated, the operation amount cannot be input. Part of L4 in FIG. 17, indicated by a broken line, indicates that even when the switch of the second input unit 323 is pressed, the signal therefrom cannot be input.

Figure 17:
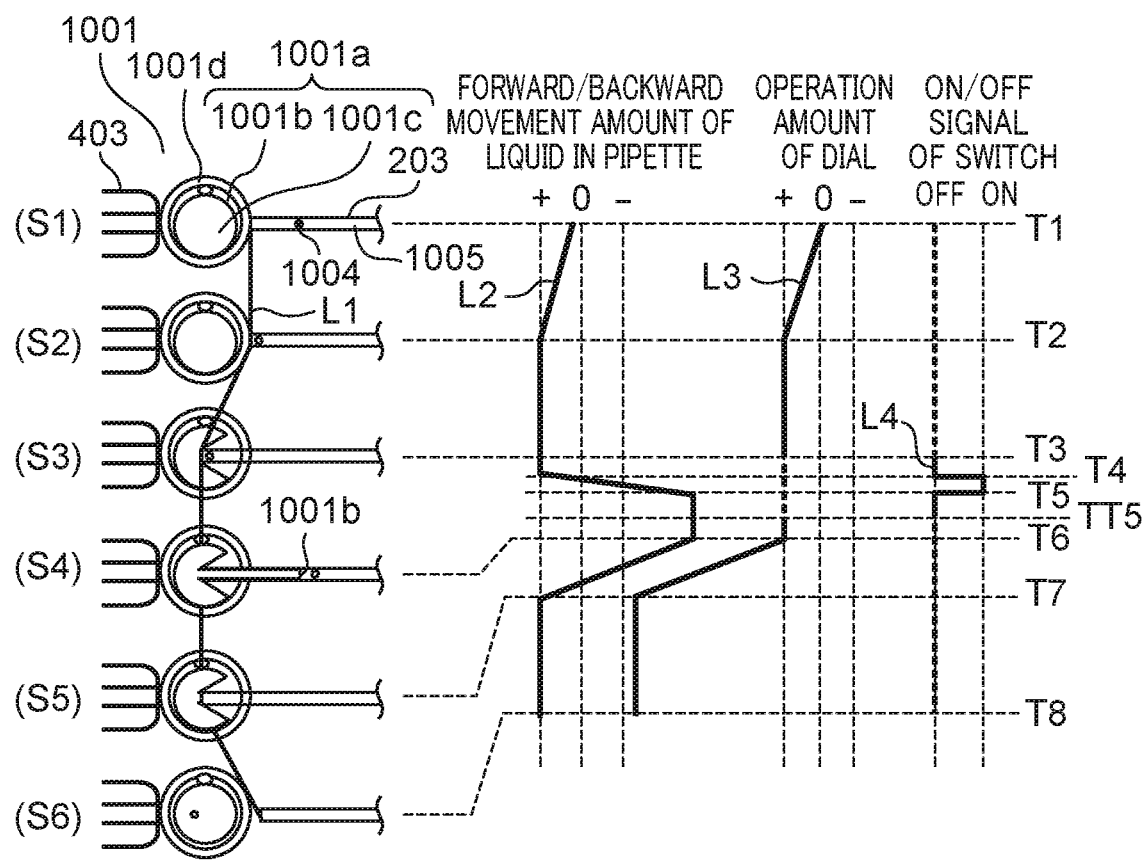
FIG. 17 is a diagram useful in explaining an operation procedure of an ovum cell membrane breaking operation in a sixth embodiment.

First, in steps S1 to S3 in FIG. 17, the operator sets the switching unit such that the first input unit 302 can be operated. This disables the second input unit 323 from inputting a signal, so that the injector device can be operated only in the first operation mode H1.

In a step S3 in FIG. 17, when the injection pipette 203 has been pressed into the ovum cell 1001a, the operator sets the switching unit such that the second input unit 323 is capable of inputting a signal (T3). This disables the the first input unit 302 from being operated, so that the injector device can be operated only in the second operation mode H2, J2, or K2.

So, the on-signal is input to the second input unit 323 (T4). With this, the linear moving unit 306 drives the piston 305 at a predetermined acceleration to suck the liquid 1005 into the injection pipette 203 at a proper speed and break the ovum cell membrane 1001b.

After that, when it is confirmed that the linear moving unit 306 has stopped, the operator operates the switching unit again to enable the first input unit 302 to be operated and disable the second input unit 323 from inputting a signal (TT5). That is, the injector device is shifted to a state operable only in the first mode H1. Then, the operator operates the first input unit 302 to inject the sperm 1004 (T6).

Therefore, in the seventh embodiment, by using the switching unit, the injector device is prevented from shifting to a state in which an operation in the first operation mode H1 and an operation in the second operation mode H2, J2, or K2 are enabled at the same time.

As described above, although in the fourth to sixth embodiments, an input operation in the first operation mode and an input operation in the second operation mode can be simultaneously performed, in the seventh embodiment, the injector device is prevented from being operable in the first operation mode and the second operation mode at the same time. Therefore, the seventh embodiment is more advantageous than the sixth embodiment in the effect that the injector device makes it possible to perform the membrane breaking operation without requiring a skilled technique dependent on visual determination and operation skill of performed of an operator. This enables an operator who is less experienced in the membrane breaking operation to easily perform desired processing with high accuracy.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-017988, filed Feb. 4, 2019, Japanese Patent Application No. 2018-228914, filed Dec. 6, 2018 and Japanese Patent Application No. 2018-228915, filed Dec. 6, 2018, which are hereby incorporated by reference herein in their entirety.

What is claimed is:

1. A stage device comprising:
a vibration actuator including a vibration element having an elastic body and an electromechanical energy conversion element, and a contact body in contact with the vibration element, one of the vibration element and the contact body being fixed at a predetermined position, and the other being a movable body which is movable in a predetermined direction and is also connected to an object to be driven, the vibration actuator being configured to drive the object to be driven in the predetermined direction; and
a control unit configured to perform control such that the movable body is moved or vibrated in the predetermined direction by applying two-phase AC voltages to the electromechanical energy conversion element to thereby excite predetermined vibrations in the vibration element,
wherein the control unit causes the vibration actuator to be driven such that an operation mode is switched between a movement mode for moving the object to be driven in the predetermined direction and a vibration mode for vibrating the object to be driven in the predetermined direction,
wherein an absolute value of a phase difference between the two-phase AC voltages in the movement mode is larger than 0° and not larger than 90°, and
wherein the phase difference between the two-phase AC voltages in the vibration mode is +180° or −180°.

2. The stage device according to claim 1, wherein the vibration element has protrusions provided on the elastic body and in contact with the contact body, and
wherein the control unit causes
the movable body to be moved, in the movement mode, in the predetermined direction, using thrust which is given to the contact body by a circular motion or an elliptical motion on a tip end of each of the protrusion generated by applying two-phase AC voltages to the electromechanical energy conversion element, and
the movable body to be vibrated, in the vibration mode, in the predetermined direction, using thrust which is given to the contact body by a reciprocating motion on the tip end of each of the protrusions generated applying two-phase AC voltages to the electromechanical energy conversion element.

3. The stage device according to claim 2, wherein the control unit causes a magnitude of the two-phase AC voltages to be changed in the vibration mode.

4. The stage device according to claim 2, wherein the control unit causes a frequency of the two-phase AC voltages to be changed between the movement mode and the vibration mode.

5. A minute operation device comprising:
an object to be driven;
a vibration actuator including a vibration element having an elastic body and an electromechanical energy conversion element, and a contact body in contact with the vibration element, one of the vibration element and the contact body being fixed at a predetermined position, and the other being a movable body which is movable in a predetermined direction and is also connected to the object to be driven, the vibration actuator being configured to drive the object to be driven in the predetermined direction; and
a control unit configured to perform control such that the movable body is moved or vibrated in the predetermined direction by applying two-phase AC voltages to the electromechanical energy conversion element to thereby excite predetermined vibrations in the vibration element,
wherein the control unit causes the vibration actuator to be driven such that an operation mode is switched between a movement mode for moving the object to be driven in the predetermined direction and a vibration mode for vibrating the object to be driven in the predetermined direction,
wherein an absolute value of a phase difference between the two-phase AC voltages in the movement mode is larger than 0° and not larger than 90°, and
wherein the phase difference between the two-phase AC voltages in the vibration mode is +180° or −180°.

6. The minute operation device according to claim 5, wherein the vibration element has protrusions provided on the elastic body and in contact with the contact body, and
wherein the control unit causes
the movable body to be moved, in the movement mode, in the predetermined direction, using thrust which is given to the contact body by a circular motion or an elliptical motion on a tip end of each of the protrusion generated by applying two-phase AC voltages to the electromechanical energy conversion element, and the movable body to be vibrated, in the vibration mode, in the predetermined direction, using thrust which is given to the contact body by a reciprocating motion on the tip end of each of the protrusions generated applying two-phase AC voltages to the electromechanical energy conversion element.

7. The minute operation device according to claim 5, wherein the object to be driven is an injection pipette or a holding pipette.

8. A method of controlling a minute operation device that drives a vibration actuator including a vibration element having an elastic body and an electromechanical energy conversion element, and a contact body in contact with the vibration element, one of the vibration element and the contact body being fixed at a predetermined position, and the other being a movable body which is movable in a predetermined direction and is also connected to an object to be driven, to thereby drive the object to be driven in the predetermined direction, the method comprising:

moving the object to be driven to a predetermined position by driving the movable body through application of two-phase AC voltages to the electromechanical energy conversion element to thereby excite predetermined vibrations in the vibration element; and vibrating, in a state in which the object to be driven is in the predetermined position, the object in the predetermined position in the predetermined direction through application of two-phase AC voltages to the electromechanical energy conversion element to thereby vibrate the vibration element in the predetermined direction, wherein an absolute value of a phase difference between the two-phase AC voltages in the movement mode is larger than 0° and not larger than 90°, and wherein the phase difference between the two-phase AC voltages in the vibration mode is +180° or −180°.

9. The method according to claim 8, wherein the vibration element has protrusions provided on the elastic body and in contact with the contact body, and the method further comprising:

causing the movable body to be moved, in the movement mode, in the predetermined direction, using thrust which is given to the contact body by a circular motion or an elliptical motion on a tip end of each of the protrusion generated by applying two-phase AC voltages to the electromechanical energy conversion element, and causing the movable body to be vibrated, in the vibration mode, in the predetermined direction, using thrust which is given to the contact body by a reciprocating motion on the tip end of each of the protrusions generated applying two-phase AC voltages to the electromechanical energy conversion element.

* * * * *